US009833446B2

(12) United States Patent
Yang et al.

(10) Patent No.: US 9,833,446 B2
(45) Date of Patent: Dec. 5, 2017

(54) HEDGEHOG PATHWAY INHIBITION FOR CARTILAGE TUMOR AND METACHONDROMATOSIS TREATMENT

(71) Applicants: Rhode Island Hospital, Providence, RI (US); University Health Network, Toronto (CA)

(72) Inventors: Wentian Yang, Pawtucket, RI (US); Benjamin G. Neel, Toronto (CA)

(73) Assignees: Rhode Island Hospital, Providence, RI (US); University Health Network, Toronto (CA)

( * ) Notice: Subject to any disclaimer, the term of this patent is extended or adjusted under 35 U.S.C. 154(b) by 0 days.

(21) Appl. No.: 14/386,326

(22) PCT Filed: Mar. 14, 2013

(86) PCT No.: PCT/US2013/031396
§ 371 (c)(1),
(2) Date: Sep. 18, 2014

(87) PCT Pub. No.: WO2013/142261
PCT Pub. Date: Sep. 26, 2013

(65) Prior Publication Data
US 2015/0045363 A1    Feb. 12, 2015

Related U.S. Application Data

(60) Provisional application No. 61/614,449, filed on Mar. 22, 2012.

(51) Int. Cl.
*A61K 31/454*    (2006.01)
*A61K 31/438*    (2006.01)
(Continued)

(52) U.S. Cl.
CPC ........ *A61K 31/454* (2013.01); *A61K 31/4184* (2013.01); *A61K 31/438* (2013.01);
(Continued)

(58) Field of Classification Search
CPC .............. A61K 31/454; A61K 31/4418; A61K 31/4355; A61K 31/517; A61K 31/5377;
(Continued)

(56) References Cited

U.S. PATENT DOCUMENTS

| 7,709,454 B2 | 5/2010 | Ruiz I Altaba et al. |
| 2014/0309138 A1* | 10/2014 | Poetter ..................... C12Q 1/70 506/9 |
| 2016/0008388 A1* | 1/2016 | Brown ............... A61K 31/7048 424/278.1 |

FOREIGN PATENT DOCUMENTS

| WO | WO-2010085654 A1 | 7/2010 |
| WO | WO-2013142261 A1 | 9/2013 |

OTHER PUBLICATIONS

Onishi et al.; "Hegehog signaling pathway as a therapeutic target in various types of cancer"; Oct. 2011; 102(10): 1756-1760.*
(Continued)

*Primary Examiner* — Timothy Thomas
(74) *Attorney, Agent, or Firm* — Mintz Levin Cohn Ferris Glovsky and Popeo, P.C.; Ingrid A. Beattie

(57) ABSTRACT

A method for preventing, slowing, or blocking the formation of an exostosis or an enchondromas comprising administering to an animal in need thereof a hedgehog pathway inhibitor such as a Smoothened inhibitor.

13 Claims, 19 Drawing Sheets

(51) Int. Cl.
| | |
|---|---|
| A61K 31/4402 | (2006.01) |
| A61K 31/4184 | (2006.01) |
| A61K 31/4436 | (2006.01) |
| A61K 31/496 | (2006.01) |
| A61K 31/4545 | (2006.01) |
| A61K 31/517 | (2006.01) |
| A61K 31/5377 | (2006.01) |
| A61K 31/4355 | (2006.01) |
| A61K 31/4418 | (2006.01) |

(52) U.S. Cl.
CPC ...... *A61K 31/4355* (2013.01); *A61K 31/4402* (2013.01); *A61K 31/4418* (2013.01); *A61K 31/4436* (2013.01); *A61K 31/4545* (2013.01); *A61K 31/496* (2013.01); *A61K 31/517* (2013.01); *A61K 31/5377* (2013.01)

(58) Field of Classification Search
CPC .............. A61K 31/4436; A61K 31/496; A61K 31/4545; A61K 31/4184; A61K 31/438; A61K 31/4402
See application file for complete search history.

(56) References Cited

OTHER PUBLICATIONS

Tiet et al.; "Constitutive Hedgehog Signaling in Chondrosarcoma Up-Regulates Tumor Cell Proliferation"; 2006; Am. J. Pathol.; 168: 321-330.*
Pansuriya et al.; "Enchondromatosis: insights on the different subtypes"; 2010Int. J. Clin. Exp. Pathol.; 3(6): 557-569.*
Bowen et al.; "Loss-of-Function Mutations in PTPN11 Cause Metachondromatosis, but Not Oilier Disease or Muffacci Syndrome"; 2011; PLoS Genet 7(4): e1002050; 1-11.*
Munchhof et al.; "Discovery of PF-044499913, a Potent and Orally Bioavailable Inhibitor of Smoothened"; Dec. 21, 2011; ACS Med. Chem. Lett.; 2012; 3: 106-111.*
Pansuriya et al. "Enchondromatosis: Insights on the Different Subtypes." *Int. J. Clin. Exp. Pathol.* 3.6(2010):557-569.
Adler. Differential diagnosis of cartilage tumors. Pathol Res Pract. Dec. 1979;166(1):45-58.
Bovee et al., Cartilage tumours and bone development: molecular pathology and possible therapeutic targets. Nat Rev Cancer. Jul. 2010;10(7):481-8.
Bowen et al., Loss-of-function mutations in PTPN11 cause metachondromatosis, but not Ollier disease or Maffucci syndrome. PLoS Genet. Apr. 2011;7(4):e1002050.
Chan et al., PTPN11 is the first identified proto-oncogene that encodes a tyrosine phosphatase. Blood. Feb. 1, 2007;109(3):862-7.
Chan et al., The tyrosine phosphatase Shp2 (PTPN11) in cancer. Cancer Metastasis Rev. Jun. 2008;27(2):179-92.
Kennedy. Metachondromatosis. Radiology. Jul. 1983;148(1):117-8.
Nakamura et al., Estrogen prevents bone loss via estrogen receptor alpha and induction of Fas ligand in osteoclasts. Cell. Sep. 7, 2007;130(5):811-23.
Pannier et al., Hereditary multiple exostoses and enchondromatosis. Best Pract Res Clin Rheumatol. Mar. 2008;22(1):45-54.
Sobreira et al., Whole-genome sequencing of a single proband together with linkage analysis identifies a Mendelian disease gene. PLoS Genet. Jun. 17, 2010;6(6):e1000991.
Soriano. Generalized lacZ expression with the ROSA26 Cre reporter strain. Nat Genet. Jan. 1999;21(1):70-1.
Srinivas et al., Cre reporter strains produced by targeted insertion of EYFP and ECFP into the ROSA26 locus. BMC Dev Biol. 2001;1:4.
Yang et al., An Shp2/SFK/Ras/Erk signaling pathway controls trophoblast stem cell survival. Dev Cell. Mar. 2006;10(3):317-27.

* cited by examiner

FIG. 6C  Ctsk-Control/YFP
Ctsk-KO/YFP

Average number of exostoses (+SD)

| Treatment | Vehicle | SMOi | (p) |
|---|---|---|---|
| Posterior Paw | 4.3+1.25 | 3.1+1.1 | <0.012* |
| Knee | 2.6+0.96 | 2+0.67 | <0.025* |
| tibiae | 1.6+0.97 | 1.2+0.78 | >0.05 |

Exostoses formed at individual bone post vehicle treatment

| n | 1 | 2 | 3 | 4 | 5 | 6 | 7 | 8 | 9 | 10 | Average |
|---|---|---|---|---|---|---|---|---|---|---|---|
| Posterior Paw | 5 | 4 | 7 | 3 | 5 | 4 | 3 | 5 | 4 | 3 | 4.3 |
| Knee | 3 | 2 | 3 | 4 | 2 | 2 | 3 | 2 | 1 | 4 | 2.6 |
| Tibiae | 2 | 1 | 2 | 0 | 1 | 3 | 1 | 2 | 1 | 3 | 1.6 |

Exostoses formed at individual bone post SMOi treatment

| n | 1 | 2 | 3 | 4 | 5 | 6 | 7 | 8 | 9 | 10 | Average |
|---|---|---|---|---|---|---|---|---|---|---|---|
| Posterior Paw | 5 | 2 | 3 | 2 | 5 | 3 | 3 | 2 | 3 | 3 | 3.1 |
| Knee | 2 | 2 | 3 | 2 | 1 | 2 | 3 | 2 | 1 | 2 | 2 |
| Tibiae | 2 | 1 | 2 | 0 | 1 | 0 | 1 | 2 | 1 | 2 | 1.2 |

Control    KO

Control    KO

Control    KO

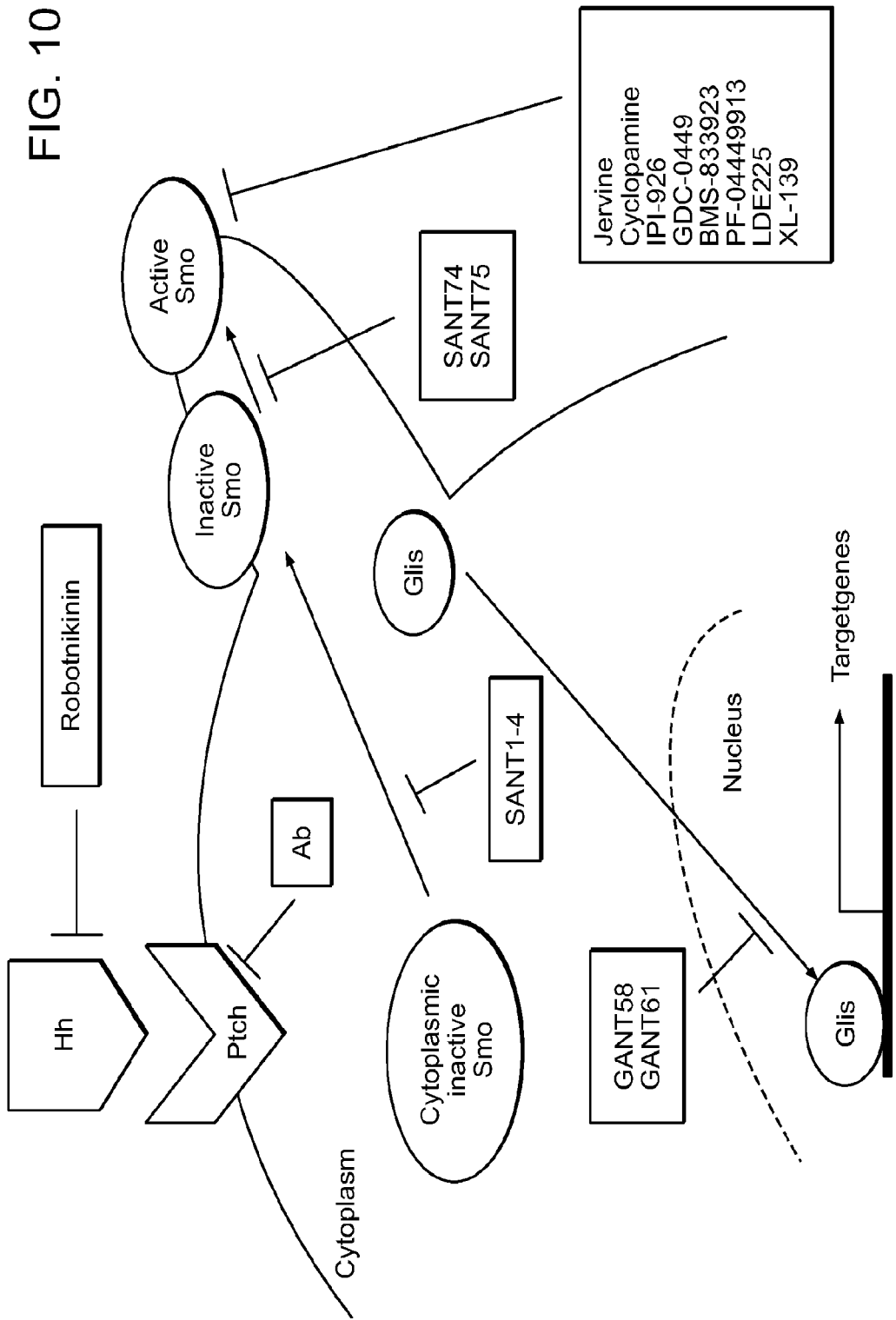

HEDGEHOG PATHWAY INHIBITION FOR CARTILAGE TUMOR AND METACHONDROMATOSIS TREATMENT

RELATED APPLICATIONS

This application is a national stage application, filed under 35 U.S.C. §371, of International Application No. PCT/US2013/031396, filed on Mar. 14, 2013, which claims priority to, and benefit of U.S. Provisional Application No. 61/614,449, filed on Mar. 22, 2012, each of which is herein incorporated by reference in its entirety.

INCORPORATION BY REFERENCE OF SEQUENCE LISTING

The contents of the text file named "21486-612001WO_ST25.txt", which was created on Apr. 24, 2013 and is 864 bytes in size, are hereby incorporated by reference in their entireties.

GOVERNMENT SUPPORT

This invention was made with Government support under NIHR21AR057156 awarded by the National Institutes of Health. The Government has certain rights in the invention.

FIELD OF THE INVENTION

The field of the invention relates to cancer therapy.

BACKGROUND OF THE INVENTION

Cartilage tumors account for 22% of all skeletal system tumors and are characterized by the formation of exostoses and/or endostoses and subsequently cause significant morbidity and mortality. Clinical treatment of cartilage tumors, such as metachondromatosis, largely relies on surgical intervention, and no effective medical therapy is currently available.

SUMMARY OF THE INVENTION

Hedgehog (Hh) pathway inhibitors, such as small molecules, e.g., PF-04449913, are used to prevent, slow, or block the formation of exostosis or enchondromas. Such compounds are also useful to prevent and/or reduce cartilage tumorigenesis such as metachondromatosis, a type of tumor caused by an autosomal dominant skeletal disorder that affects the growth of bones, leading to multiple enchondromas and osteochondromas. The latter disorder affects mainly tubular bones, though it can involve the vertebrae. The compositions and methods described herein lead to a reduction in tumor burden or tumor mass.

Exemplary Hh inhibitors include Smoothened inhibitors (SMOi). The inhibitor or combination of inhibitors is administered systemically or locally to a diseased site. Preferably, the inhibitor is a small molecule. However, proteins, peptides, antibody or antibody fragment based inhibitors are also useful. In preferred embodiments, the methods do not encompass use of MEK (MAP kinase kinase) and ERK (extracellular signal-regulated kinase) inhibitors, e.g., long term use of such inhibitors.

The methods are useful to treat human patients, as well as animals such as companion animals (e.g., dogs, cats), as well as livestock and working animals (e.g., horses, cattle, goats, sheep, chickens).

In addition to methods of treating cartilage diseases and cartilage tumors, the methods are useful to reduce or prevent development of a benign or non-malignant cartilage disorder such as metachondromatosis (a benign cartilage tumor syndrome with malignant potential) into malignant disease such as malignant chondrosarcoma.

Also within the invention is a composition, e.g., a pharmaceutical composition, comprising a cartilage tumor-inhibiting amount of a hedgehog pathway inhibitor such as a Smoothened inhibitor or Smoothened receptor inhibitor. A pharmaceutical composition includes an active therapeutic agent, e.g., small molecule inhibitor, and a pharmaceutically acceptable or physiologically acceptable excipient or inactive ingredient(s).

Compounds described herein, e.g., those used for therapy are purified and/or isolated. As used herein, an "isolated" or "purified" compound (e.g., small molecule drug), nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, or 100%, by weight the compound of interest. Purity is measured by any appropriate standard method, for example, by column chromatography, polyacrylamide gel electrophoresis, or HPLC analysis.

Publications, U.S. patents and applications, Genbank/NCBI accession numbers, and all other references cited herein, are hereby incorporated by reference.

BRIEF DESCRIPTION OF THE DRAWINGS

FIGS. 2a-d are photomicrographs showing that skeletal tumors in Ctsk-KO mice originate from Shp2-deficient chondroid cells in the perichondrial Groove of Ranvier. a, X-gal staining of knee joint sections from 1-week-old R26lacZ; Ctsk-Cre and R26lacZ; LysM-Cre reporter mice shows that the Ctsk (but not the LysM) promoter is active not only in osteoclasts, but also in a subset of cells residing in Perichondrial Groove of Ranvier. b, H&E and Safranin O staining of knee joint sections from day P10 Ctsk-Control (i,iv) and Ctsk-KO (ii, iii, v, vi) mice showing expansion of chondroid cells within the Perichondrial Groove of Ranvier region in Ctsk-KO mice (arrows). Images in iii & vi are magnified (10×) views of boxed areas in ii & v respectively; c, H&E-and Safranin O-stained section showing expanding YFP+ population within the Perichondrial Groove of Ranvier (boxed region in top panels, magnified below) that also stains with Safranin O, indicative of cartilage. d, frozen section of an exostosis from the metatarsal joint of Ctsk- KO/YFP mice showing co-localization of YFP reporter with cartilaginous tumor cells (boxed-in area). Note that the lesion contains proliferating and hypertrophic chondrocytes, as revealed by Col2α1 and Col10α1 immunostaining, respectively.

FIG. 4a, Right panel, is a series of photomicrographs showing immunostaining of paraffin sections from Perichondrial Groove of Ranvier region of Ctsk-KO and Control mice. Note the decreased number of p-Erk+ cells, but increased Ihh expression in Ctsk-KO, compared with Control, mice. FIG. 4b, Right panels, is an immunoblot and bar graph showing that Shp2 deficiency decreases Erk activation in response to Fgf18 (top), while q-PCR (bottom) shows increased Ihh and Pthrp expression in Shp2 deficient ATDC5 cells (n=3, *p<0.05, Student t test).

FIG. 6c is a series of Faxitron radiographs show that recipients of Ctsk-KO, but not Ctsk-Control, bone marrow have increased bone mineral density, but do not develop exostoses even after >12 months of observation.

FIG. 10 is a diagram of Hedgehog (Hh) signaling pathway and exemplary inhibitors, e.g., Smoothened (Smo) inhibitor (GDC-0449, IPI-926, etc.), inhibition of the transformation of inactive Smo into active Smo (SANT 74, SANT 75), inhibition of the transport of cytoplasmic inactive Smo to cilia (SANT 1-4), inhibition of binding of Gli to DNA (GANT 58, GANT 61), Shh antagonist (Robotnikinin) and anti-Patched (Ptch) antibody.

DETAILED DESCRIPTION

Figure 1A:
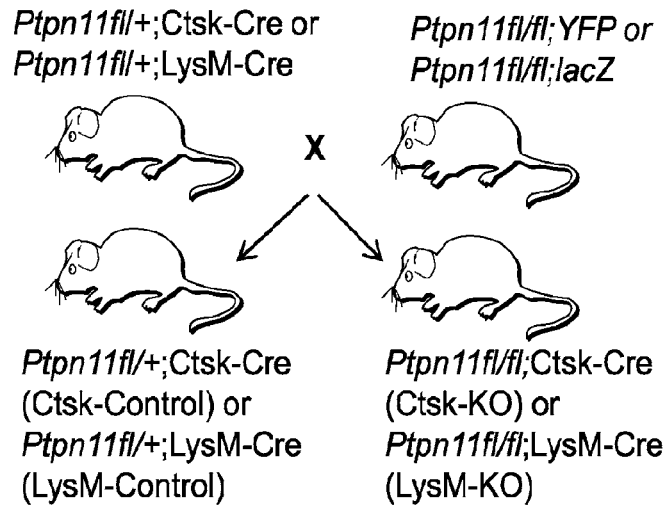
FIG. 1a is a diagram showing breeding schemes for generating Ctsk-KO, LysM-KO, and their respective Control mice.

Src-homology 2 domain-containing phosphatase 2 (SHP2) belongs to the protein-tyrosine phosphatase family of proteins. It is a member of the non-receptor class 2 subfamily and contains 2 SH2 domains and 1 tyrosine-protein phosphatase domain.

Based on tissue specific gene knockout approaches, whole-genome sequencing, and linkage analysis with high-density SNP array assays, mutations in Ptpn11 gene, encoding the src homology 2 domain-containing protein tyrosine phosphspahtases Shp2, were found to be associated with metachondromatosis (MC), a benign cartilage tumor syndrome with malignant potential. Further biological and biochemical studies uncovered that 1) It is the Ptpn11 loss-of-function mutations in a novel perichondrial cartilaginous cell population that causes metachondromatosis; 2) cartilage tumor lesions in Shp2 mutant mice express elevated levels of Indian hedgehog and parathyroid hormone related protein (PTHrP); and 3) blockade of hedgehog signaling in Shp2 mutant animals by administration of hedgehog pathway inhibitors, such as the Smoothened inhibitor PF-0444993 can stop or slow down the disease process. The data indicates that inhibition or attenuation of hedgehog pathway pharmacologically is useful to treat and prevent cartilage tumorigenesis, such as metachondromatosis (FIGS. 9A-F).

By using transgenic animals that lack Shp2 in a unique perichondrial cartilaginous cell population, elevated expression of IHH and PTHrP and ectopic hedgehog signaling in epiphyseal cartilage cells were found to play an important role in the formation of exostosis and enchondromas.

PF04449913 is a hedgehog signaling pathway inhibitor of the SMOi class. This inhibitor is orally administered and has antineoplastic activity. The inhibitor was found to block or attenuate hedgehog signaling. Systematic PF04449913 administration reduces the cartilage tumor condition developed in Shp2 mutant mice. PF04449913 is a Smoothened (Smo) inhibitor that is available from Pfizer, Inc. This small molecule and other hedgehog pathway inhibitors such as Smo inhibitors, are known in the art, e.g., Onishi et al., 2011, Cancer Science 102:1756-1760, hereby incorporated by reference. IPI-926 and GDC-0449 are the 2 leading compounds in the class. Exemplary members of the Hedgehog inhibitor class of compounds include Cyclopamine ($C_{27}H_{41}NO_2$), Jervine ($C_{27}H_{39}NO_3$), Infinity IPI-926/saridegib, Genentech GDC-0449/vismodegib, and Novartis LDE-225/erismodegib, and Millennium Pharmaceuticals's TAK-441.

For example, other Smo inhibitors include BMS-833923 (a.k.a., XL-139; Bristol-Meyers Squibb) and LDE225 (Novartis). Additional Hh pathway inhibitors are known in the art, see, e.g., FIG. 10, e.g., Cyclopamine, which suppresses the Hh signaling pathway through direct interaction with Smo; a Cyclopamine with improved solubility (IPI-926); non-cyclopamine-based Smo inhibitors (GDC-0499, LDE225, BMS-833923, XL-139, PF-0449913), inhibitors of the transformation of inactive Smo into active Smo (SANT 74-75), and inhibitors of the transport of cytoplasmic inactive Smo to cilia (SANT 1-4).

Small molecule inhibitors such as those described above are generally 1000 daltons or smaller in molecular mass, e.g., 700, 500, 250, 200, 100 daltons. Exemplary doses range from about 0.1 mg/Kg to about 1000 mg/Kg. For example, some inhibitors are administered at a dose of 10-500, e.g., 100-300 mg per day. Effective doses may vary, as recognized by those skilled in the art, depending on the types of tumors treated, route of administration, excipient usage, and co-administration with other agents. Routes of administration include systemically (e.g., orally, intravenously, or intramuscularly) or locally (e.g., by directly contacting the tumor by injection or implantation of a drug-eluting device). For treatment of metachondromatosis, oral administration is a preferred route of administration of therapeutic agent.

This discovery allows one to use hedgehog pathway inhibitors to stop or slow down the unguided chondrogenic cell proliferation and differentiation and treat metachondromatosis and other cartilage tumors. The administration of hedgehog pathway inhibitors locally or systematically to prevents, slows down, or blocks the formation of exostosis and enchondromas and treat cartilage tumorigenesis, such as metachondromatosis. Treating patients with cartilage tumors provides clinicians with an alternative and noninvasive approach to treat patients with cartilage tumors, such as metachondromatosis. The methods exclude treatment of non-cartilage tumors, hematopoetic system tumors (leukemia, lymphoma), basal cell carcinoma, brain (such as medulloblastoma), lung, pancreatic, colorectal, ovarian, gastric, glioblastoma, prostate, sarcoma, multiple myeloma, breast, leukemia, small cell lung cancer, gastric, multiple myeloma, osteosarcoma, and/or stomach/gastroesophageal cancers. In some instances, the methods exclude treatment of malignant chondrosarcoma. However, the methods are used for early treatment of cartilage tumors, e.g., benign metachondromatosis and other benign/non-malignant or pre-malignant cartilage disorders, prior to development into a malignant phenotype. Thus, early intervention at benign or pre-malignant stage of a cartilage disease or disorder reduces or prevents progression to a malignant state, thereby representing an important advantage of this therapeutic approach. Thus, the Hh inhibitor, e.g., SMOi, are administered prior to diagnosis of malignant chrondrosarcoma. Methods of diagnosing a benign/non-malignant phenotype from malignant chondrosarcoma are known in the art, e.g., by histological analysis of biopsied tissue.

Ptpn11 Deficiency in a Novel Cartilage Stem/Progenitor Cell Causes Metachondromatosis by Activating the Hedgehog Pathway SHP2, encoded by PTPN11, is required for survival, proliferation and differentiation of various cell types. Germ line activating mutations in PTPN11 cause Noonan Syndrome, while somatic PTPN11 mutations cause childhood myeloproliferative disease and contribute to some solid tumors (Chan et al., 2008, Cancer Metastasis Rev 27, 179-192; Chan et al., 2007, Blood 109, 862-867). Heterozygous inactivating mutations in PTPN11 were found in metachondromatosis, a rare inherited disorder featuring multiple exostoses, endochondromas, joint destruction and bony deformities (Bowen et al., 2011 PLoS Genet 7, e1002050; Sobreira et al., 2010, PLoS Genet 6, e1000991). The detailed pathogenesis of this disorder has remained unclear. Here, we used a conditional knockout allele (Ptpn11fl) and Cre recombinase (Cre) transgenic mice to delete Ptpn11 specifically in monocytes, macrophages and osteoclasts (lysozyme M-Cre; LysMCre) or in cathepsin K (Ctsk)-expressing cells, previously thought to be osteoclasts. LysMCre; Ptpn11$^{fl/fl}$ mice had mild osteopetrosis. Surprisingly, however, CtskCre; Ptpn11$^{fl/fl}$ mice developed features strikingly similar to metachondromatosis. Lineage tracing revealed a novel population of Ctsk-Cre-expressing cells in the "Perichondrial Groove of Ranvier" that expressed markers consistent with mesenchymal progenitors. Chondroid neoplasms arose from these cells and showed decreased Erk activation, increased Indian Hedgehog (Ihh) and Parathyroid hormone-related protein (Pthrp) expression and excessive proliferation. Shp2-deficient chondroprogenitors had decreased FGF-evoked Erk activation and enhanced Ihh and Pthrp expression, whereas FGFR or MEK inhibitor treatment of chondroid cells increased Ihh and Pthrp expression. Most importantly, Smoothened inhibitor treatment ameliorated metachondromatosis features in CtskCre; Ptpn11$^{fl/fl}$ mice. Thus, in contrast to its pro-oncogenic role in hematopoietic and epithelial cells, Ptpn11 is a tumor suppressor in cartilage, acting via an FGFR/MEK/ERK-dependent pathway in a novel progenitor cell population to prevent excessive Ihh production.

Cartilage Tumors

Cartilage tumors, which include exostoses, enchondromas and chondrosarcomas, account for ~20% of skeletal neoplasms and cause significant morbidity/mortality (Bovee, et al., 2010, Nat Rev Cancer 10, 481-488). Methods of diagnosing such tumors is well known in the art (Adler, C L, 1979, Pathol Res Pract. 166(1):45-58). Benign and malignant cartilaginous tumors arise sporadically at all ages, but there are also cartilage tumor syndromes, including hereditary multiple exostoses (HME) (Pannier et al., 2009, Best Pract Res Clin Rheumatol 22, 45-54; Pansuriya et al., 2010, Int J Clin Exp Pathol 3, 557-569)., the multiple enchondromatosis disorders (Ollier disease and Maffucci syndrome), and metachondromatosis (MC) (Kennedy, L. A., 2003, Radiology 148, 117-118). The molecular mechanisms underlying the development and progression of most cartilage tumors remain incompletely understood.

MC is an autosomal dominant tumor syndrome featuring multiple exostoses and enchondromas. Recently, disease-associated whole-genome sequencing and linkage analysis using high-density SNP arrays uncovered heterogyzous early frameshift or nonsense mutations in PTPN11 in >50% of MC cases. PTPN11 encodes the non-receptor protein-tyrosine phosphatase SHP2, which is required for RAS/ERK pathway activation in most receptor tyrosine kinase (RTK), cytokine receptor, and integrin signaling pathways1,2. Germ line activating mutations in PTPN11 cause Noonan syndrome (NS), whereas PTPN11 mutations that substantially impair SHP2 catalytic activity cause LEOPARD syndrome (LS), both of which show incompletely penetrant skeletal abnormalities. Somatic activating mutations in PTPN11 are the most common cause of the childhood myeloproliferative disease juvenile myelomyelogenous leukemia (JMML) and contribute to several solid tumors. Although PTPN11 is a well established human oncogene, prior to the invention it was unclear how heterozygous loss-of-function PTPN11 alleles cause the cartilage neoplasms in MC.

The following materials and methods were used to generate the data described herein.

Mice. Ptpn11 floxed (Ptpn11fl) (Yang et al. 2006, Dev Cell 10, 317-327), cathepsin K-Cre (CtskCre) (Nakamura et al., 2007, Cell 130, 811-823, Roza26lacZ (R26lacZ) (Soriano et al., 1999, Nat Genet 21, 70-71), and Rosa26EYFP (YFP) (Srinivas et al., 2001, BMC Dev Biol 1, 41). Cre reporter mice have been described previously. All mice were analyzed on the C57BL/6 background. PCR genotyping was performed using known methods. Antibodies and Reagents. The following antibodies were purchased: monoclonal anti-phospho(p)-tyrosine (4G10) was from Millipore; polyclonal antibodies against phospho(p)-Erk1/2, Erk2, p-Akt(Ser473), Akt, Shp2, p-Stat1(Tyr701) and Stat1 were from Cell Signaling Inc.; antibodies against Ihh, Col2α1, and Col10α1 were from Santa Cruz Biotechnology and ABcam, respectively; polyclonal antibodies against YFP were from Invitrogen; and fluorescence-labeled antibodies against CD31, CD44, CD45, CD90, and CD166 were purchased from eBioscience. FGF18 was purchased from Peprotech Inc. UO126 and PD173074 was from Calbiochem and Selleck-bio respectively. PF-04449913 was obtained from Pfizer, Inc.

Cell isolation and cultures. To isolate YFP+ cartilage cells (CCPs), epiphyseal cartilage was dissected from 2-week-old Ctsk-Control/YFP and Ctsk-KO/YFP mice, digested with hyaluronidase (2.5 mg/ml, Sigma) and Trypsin-EDTA (0.25%, Invitrogen) to remove soft tissues, and then with collagenase D (2.5 mg/ml, Roche) to release all cartilage cells.

After washing in PBS, cartilage cells were either analyzed by flow cytometry or YFP+ cells were purified by FACS and placed in short-term cultures of murine mesenchymal culture medium (StemCell Technologies Inc.) containing 10% FBS.

Parental ATDC5 cells were purchased from the ATCC and cultured in complete DMEM/F12 medium (1:1) (Invitrogen) as described46. ATDC5 cells stably expressing short hairpin RNAs against murine Shp2 (oligoA:5'GATCCCCGATTCAGAACACTGGGGACT-TCAAGAGAGTCCCCAGTGT TCTGAATCTT TTTG-GAAA (SEQ ID NO:1));
Oligo B: 5-GATCCCCGATTCAGAACACTGGGGACT-TCAAGAGAGTCCC CAGTGTTCTGAATCTTTTTG-GAAA (SEQ ID NO:2)) or its scrambled control were established by using pSuper(retro)/puro retroviral vector (Oligoengine, Inc) and pEcopac.

Quantitative RT-PCR. RNA was extracted from cultured cells or cartilage lesions captured by laser dissection by using the RNeasy kit (Qiagen). cDNA was synthesized using iScript™cDNA Synthesis Kit (Bio-Rad) and q-PCR was performed by using the RT2SYBR®Green qPCR kit. All values were normalized to Gapdh levels, and qPCR data are expressed as fold-increases compared with controls.

Flow Cytometry and FACS. Epiphyseal cartilage cells were stained with fluorescence-labeled antibodies as described47 and analyzed on a BD™ LSR II flow cytometer. YFP+ cells were purified by FACS using a BD Influx™ cell sorter (BD Bioscience, San Diego, Calif.). All flow cytometric data were analyzed with FlowJo software (TreeStar).

Histology. Ctsk-Control and KO mice were euthanized at the indicated ages, and femurs, tibiae, and paws were removed and fixed in 4% paraformaldehyde (PFA) overnight at 4° C. Postnatal skeletal tissues were decalcified in 0.5M EDTA before embedding. Tissue sections (5 μm) were stained with Hematoxylin & Eosin (H&E), Alcian blue, or Safranin O. Immunohistochemical staining was performed using fluorescence- or peroxidase-coupled anti-rabbit, mouse, or -goat secondary antibodies, as per the manufacturer's instructions, with Diaminobenzidine (DAB) serving as the substrate. X-gal staining was performed using known methods.

Microcomputed Tomography (μ-CT) and x-Ray Analysis. X-ray images of the entire skeleton, knees, metatarsals and phalanges were obtained immediately after euthanasia by using a Faxitron X-ray system (Wheeling, Ill.). After fixation in 4% PFA, μ-CT images of skeletal tissues were scanned with the desktop microcomputer graphic imaging system (μ-CT40, Scanco Medical AG, CH). The number and size of exostoses were measured visually based on x-ray images.

Immunoblotting. Cells were lysed in NP-40 buffer (0.5% NP40, 150 mM NaCl, 1 mM EDTA, 50 mM Tris [pH 7.4]), supplemented with a protease inhibitor cocktail (1 mM PMSF, 1 mM NaF, 1 mM sodium orthovanadate, 10 mg/ml aprotinin, 0.5 mg/ml antipain, and 0.5 mg/ml pepstatin), as described17. For immunoblotting, cell lysates (10-50 μg) were resolved by SDS-PAGE, transferred to PVDF membranes, and incubated with primary antibodies for 2 hr or overnight at 4° C. (according to the manufacturer's instructions), followed by HRP-conjugated secondary antibodies. Detection was by enhanced chemiluminescence (Amersham).

Statistical Analysis. Differences between groups were evaluated by Student t test or x2 test, as indicated. A p value of <0.05 was considered significant. All analyses were performed by using Excel (Microsoft, Redmond, Wash.) and Prism 3.0 (GraphPad, San Diego, Calif.).

Cellular Context-Specific Tumor Suppression by Ptpn11

Global deletion of mouse Ptpn11 results in early embryonic lethality, whereas postnatal deletion has context-dependent effects on tissue development and function. To assess the role of Shp2 in osteoclasts (OC), we crossed Ptpn11fl mice17 to transgenic mice expressing Cre under the control of the endogenous lysozyme M (LysM)-18 or cathepsin K19 (Ctsk)-promoter. These crosses generated Ptpn11fl/+; LysM-Cre and Ptpn11fl/fl; LysMCre (hereafter, LysM-Control and LysM-KO) and Ptpn11fl/+; CtskCre and Ptpn11fl/fl; CtskCre (hereafter, Ctsk-Control and Ctsk-KO) (FIG. 1a) mice, respectively. Neither Ptpn11fl/+; LysMCre, nor Ptpn11fl/+; CtskCre, mice had a discernible phenotype, so we focused all subsequent analyses on LysM-KO and Ctsk-KO mice.

Figure 1B:
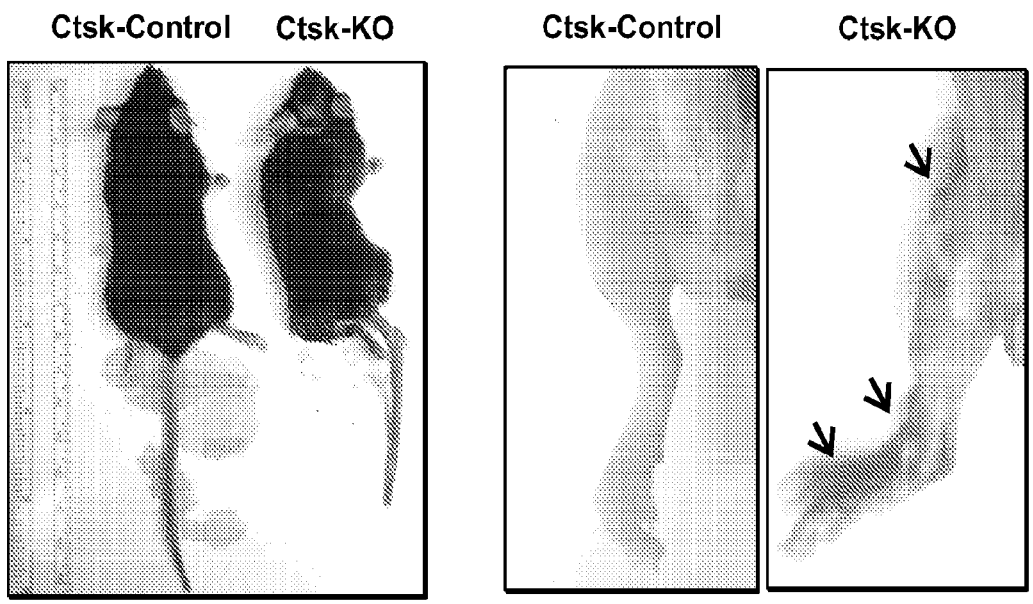
FIG. 1d is a series of photomicrographs showing sagittal sections of metatarsal joints stained with H&E (i-iii), Safranin O (iv-vi) and Alcian blue (vii-ix) showing cartilaginous exostoses and enchondromas (arrows) in Ctsk-KO mice. Images in iii, vi and ix are magnified (10×) views of boxed areas in ii, iv and viii, respectively. These data show that Ptpn11 deletion in Cathepsin K-expressing cells causes metachondromatosis.
Figure 1C:
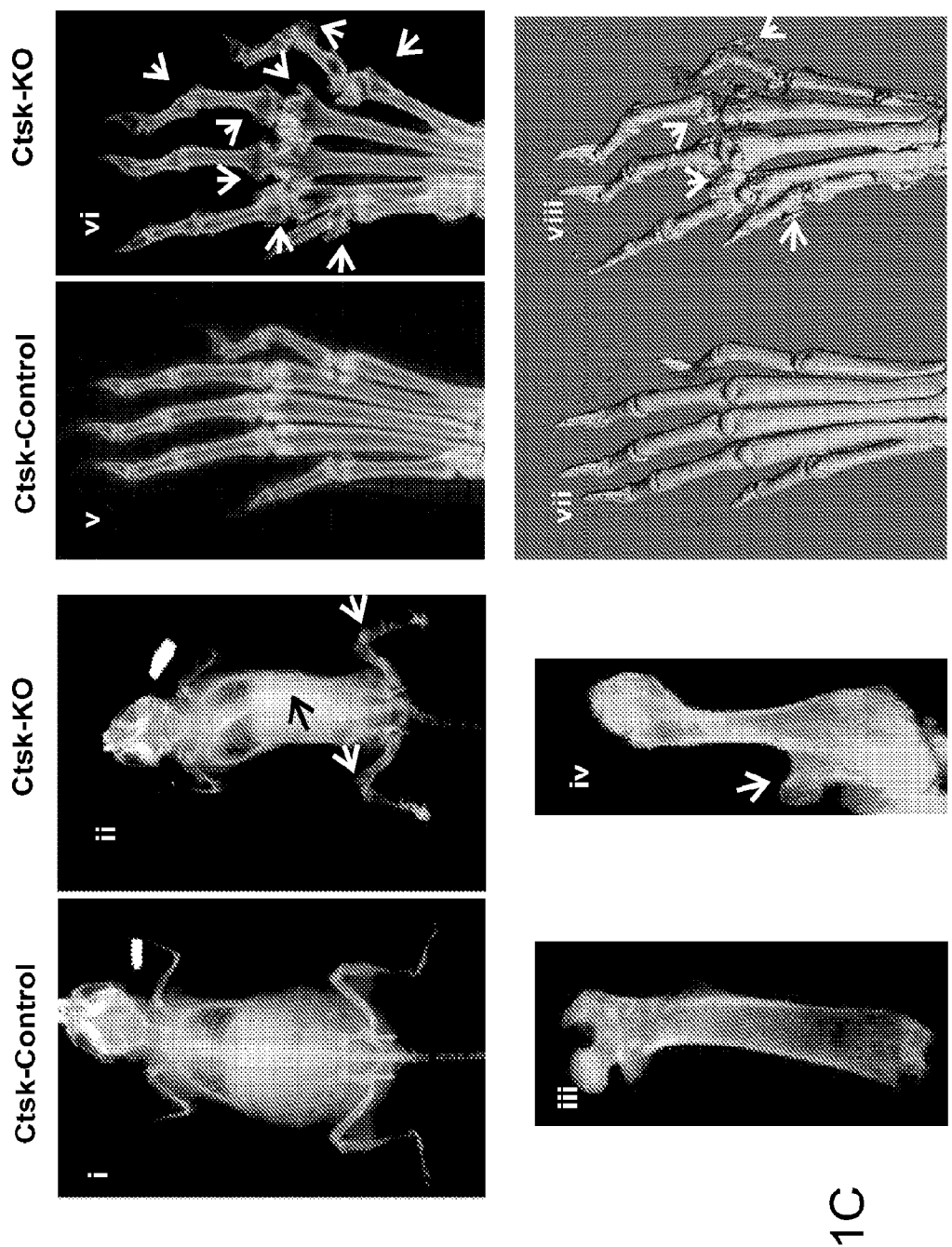
Figure 1D:
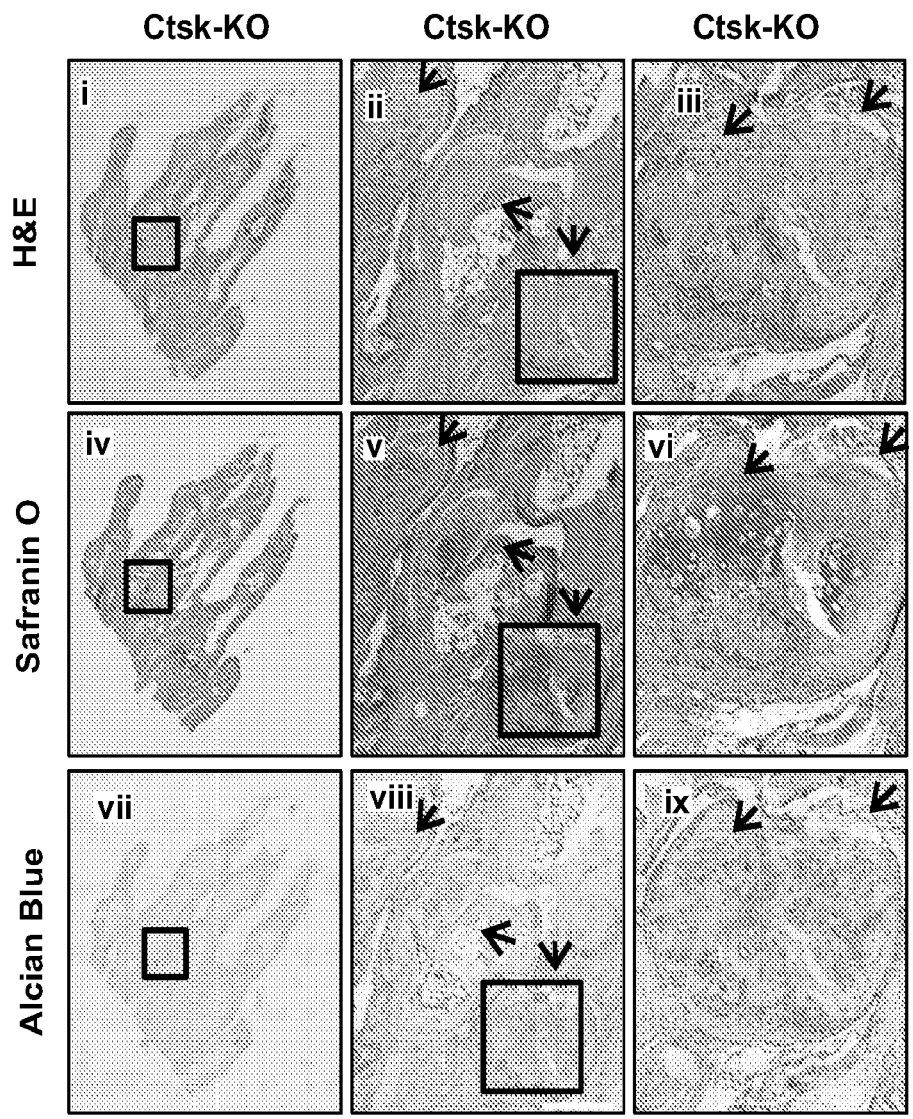
Figure 5B:
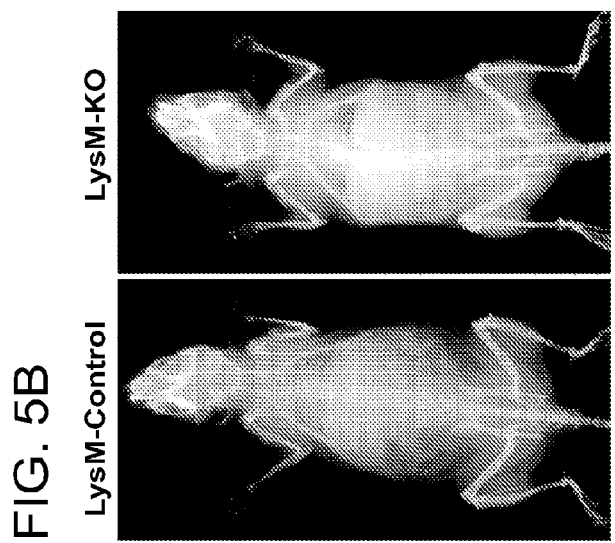
FIG. 5b is a series of Faxitron radiographs that demonstrate increased bone mineral density in LysM-KO mice compared with Controls, but no exostoses or joint deformation.
Figure 5A:
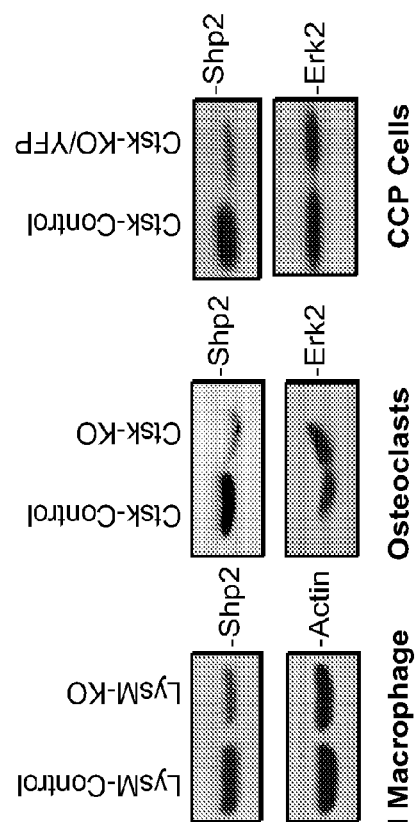
FIG. 5a is a series of immunoblots showing Shp2 levels in bone marrow-derived macrophages (left), osteoclasts (middle), and in YFP+ perichondrial cells (CCPs) (right) from Ctsk-Control/YFP and KO/YFP mice, as indicated; Erk2 levels serve as a loading control.
Figure 5C:
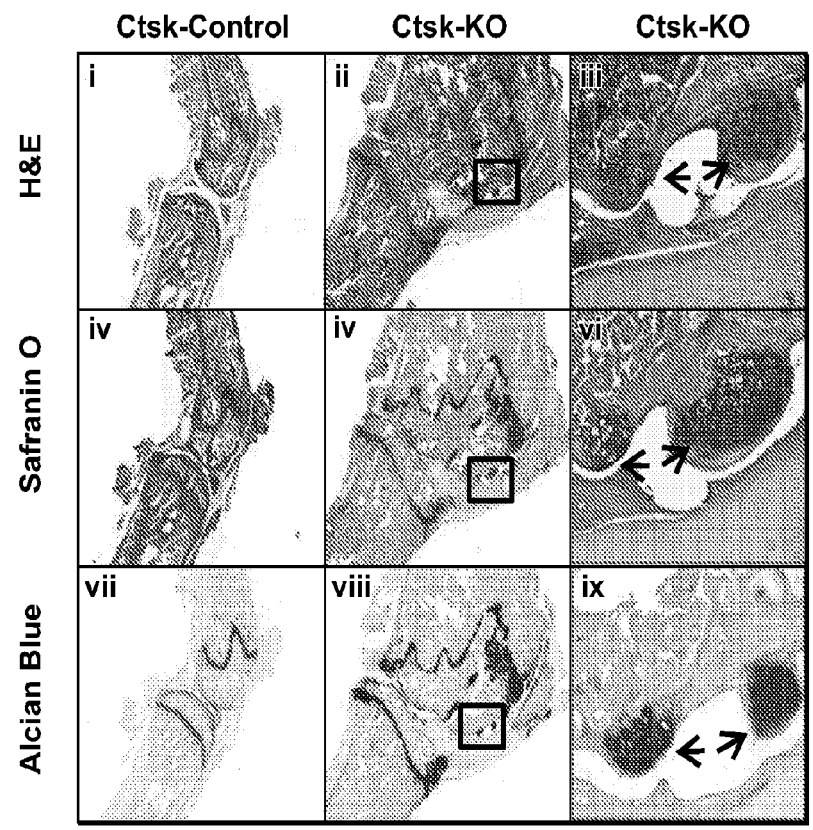
FIG. 5c is a series of photomicrographs showing H&E-(i-iii), Safranin O-(iv-vi) and Alcian blue (vii-ix) staining of sagittal sections of knee joints from 12-week-old Ctsk-Control (i, iv, vii) and Ctsk-KO (ii, iii, v, vi, viii, ix) mice. Image iii, vi & ix are magnified views (10×) of the boxed areas in ii, v, and viii, respectively. Note exostoses (arrows) in Ctsk-KO mice. Compared with Controls, Ctsk-KO mice have markedly enlarged distal femurs and proximal tibiae and elongated metaphyses with a broad and coast shape-like growth plate cartilage (ii, v, viii). Newly forming cartilage masses are seen readily at the epiphyses (iii, vi, ix).
Figure 5D:
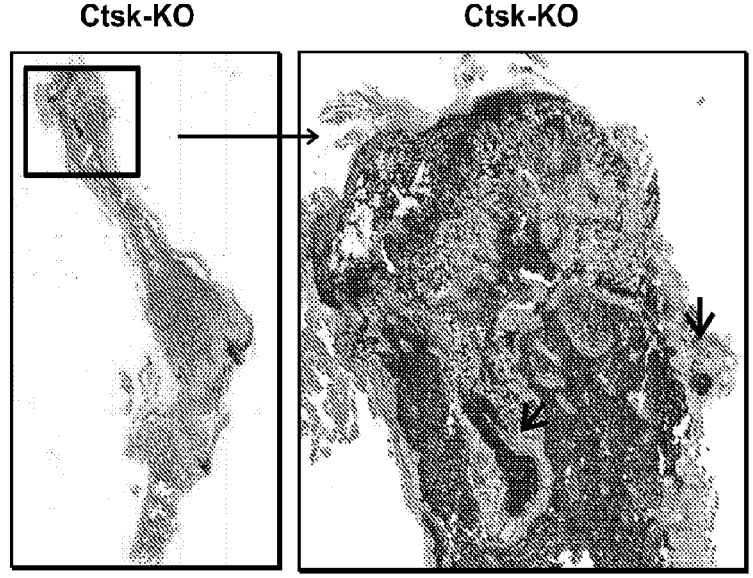
FIG. 5d is a series of photomicrographs of Safranin O stain showing enchondromas (arrows) in tubular bones of Ctsk-KO mice.

The LysM promoter is active in monocytes, macrophages and osteoclast precursors, whereas the Ctsk promoter reportedly is active only in mature OC. As expected, Shp2 levels were reduced by >80% in bone marrow-derived macrophages (BMM) and OC in LysM-KO and Ctsk-KO mice (FIG. 5a). LysM-KO and Ctsk-KO mice were born at the expected Mendelian ratios and appeared normal for their first 3 weeks post-birth. Subsequently, LysM-KO mice developed mild, age-related osteopetrosis (FIG. 5b). By contrast, Ctsk-KO mice exhibited a dramatic skeletal phenotype, comprising decreased body length, increased bone mineral density, scoliosis, exostoses at the metaphyses of tubular bones (including femurs, tibiae, metatarsals, and phalanges) and rapidly decreasing mobility (FIG. 1b-d). Sections of hindlimb paw and knee joints from 12-week-old Ctsk-KO mice revealed multiple exostoses and enchondromas at the metaphyses of their metatarsals and phalanges (FIG. 1d), tibiae and femurs (FIG. 5c,d), and other bones (data not shown), features strongly resembling human MC. Given that heterozygous PTPN11 frameshift mutations cause MC5,6, our findings indicate that PTPN11 acts as a tumor suppressor gene in cartilage and strongly suggest that loss (or silencing) of the remaining PTPN11 allele is required for tumor formation in MC.

Figure 6A:
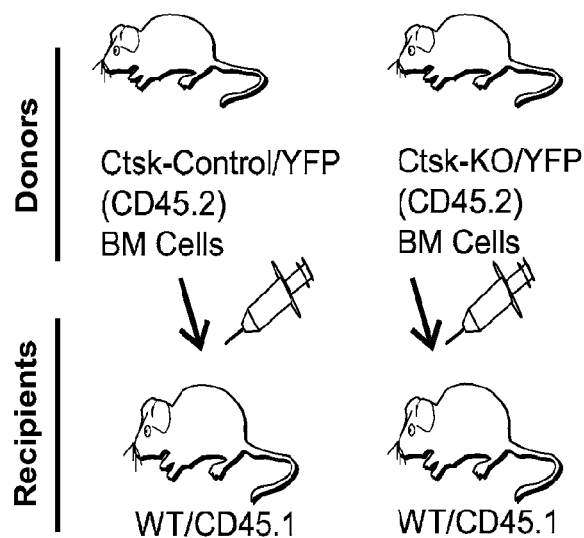
FIG. 6a is a diagram showing a scheme for using bone marrow transplantation to examine the role of osteoclasts (or other bone marrow-derived cells) in skeletal pathogenesis in Ctsk-KO mice.
Figure 6B:
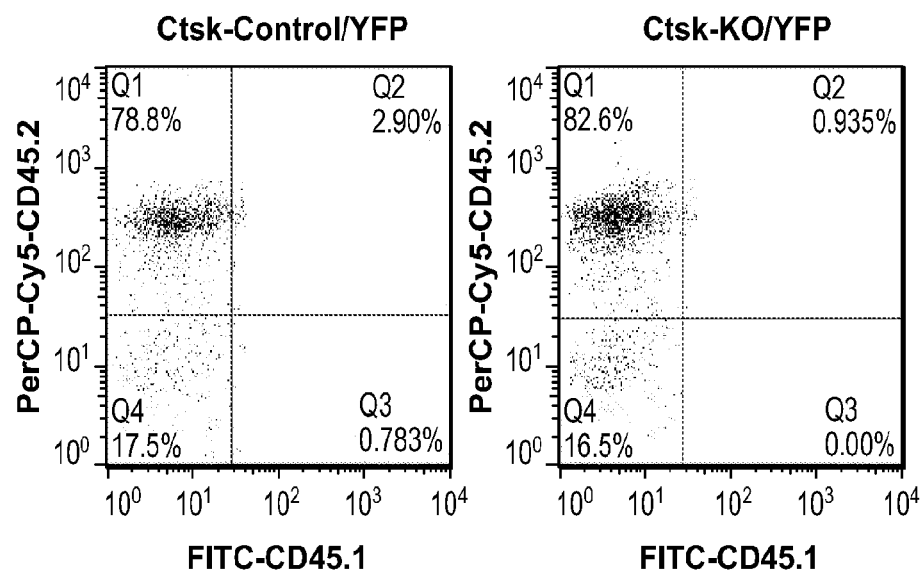
FIG. 6b is a graph showing the results of a flow cytometric analysis of peripheral blood showing high engraftment of donor BM cells from Ctsk-KO/YFP+ and Ctsk-Control/YFP+ (C57BL/6; CD45.2) mice in lethally irradiated recipients (B6.SJL; CD45.1). Tail vein bleeding was performed 12 weeks post-BMT.

To search for the cells responsible for disease in Ctsk-KO mice, we first injected bone marrow (BM) from 6-week-old Ctsk-KO and Ctsk-Control mice (C57/BL6; CD45.2) into lethally irradiated 3-week-old recipients (n=7) (B6.SJL; CD45.1). Flow cytometric analysis revealed high chimerism in the peripheral blood of all recipients (FIG. 6a,b), but no cartilage tumors developed in recipients of Ctsk-KO BM in over 12 months of observation, although they did show increased bone mineral density (FIG. 6c). Increased bone mineral density, but not cartilage neoplasia, is a consequence of defective OC development/function in Ctsk-KO mice, a conclusion consistent with the mild osteopetrosis seen in LysM-KO mice.

Figure 2A:
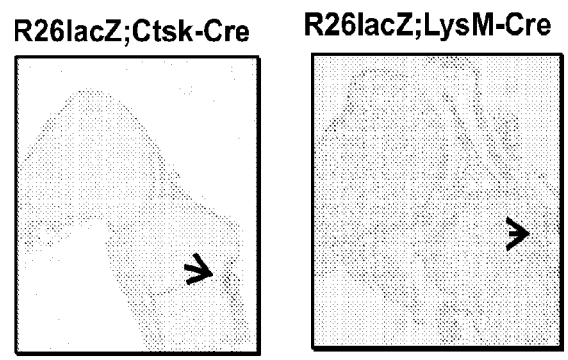
Figure 2B:
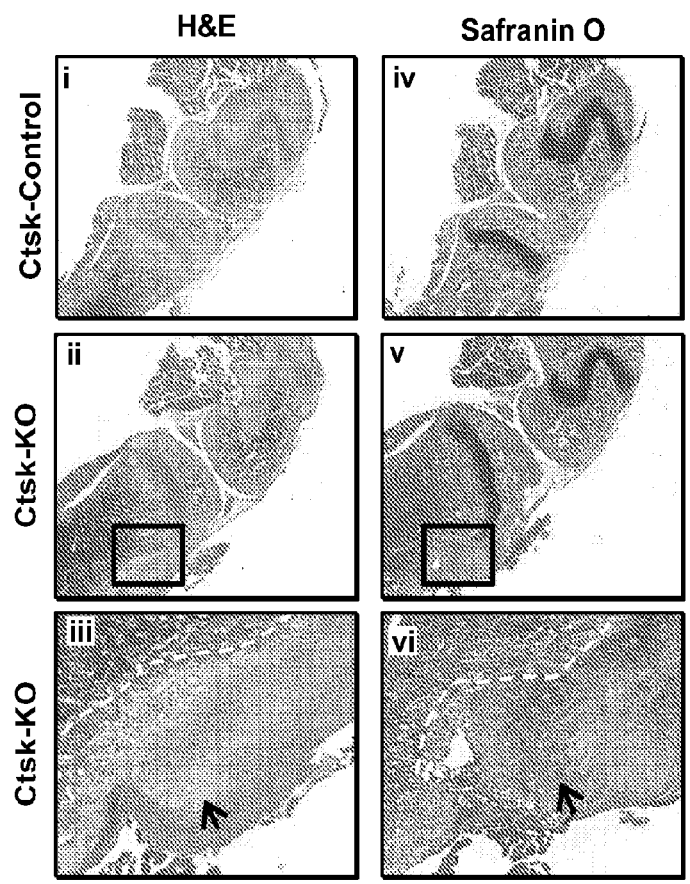
FIGS. 2b-c are photographs showing gross images (b) and Faxitron radiographs (c) of 12 week-old Ctsk-KO mice showing dwarfism, scoliosis (black arrowheads), increased bone mineral density, and multiple exostoses of knees, ankles, and metatarsals (arrowheads), accompanied by joint destruction.
Figure 2C:
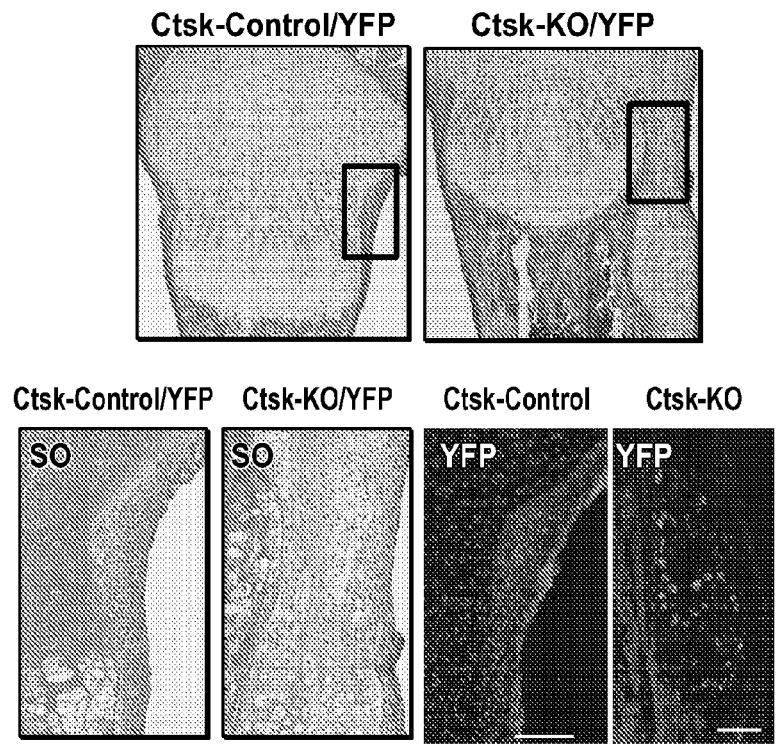
Figure 2D:
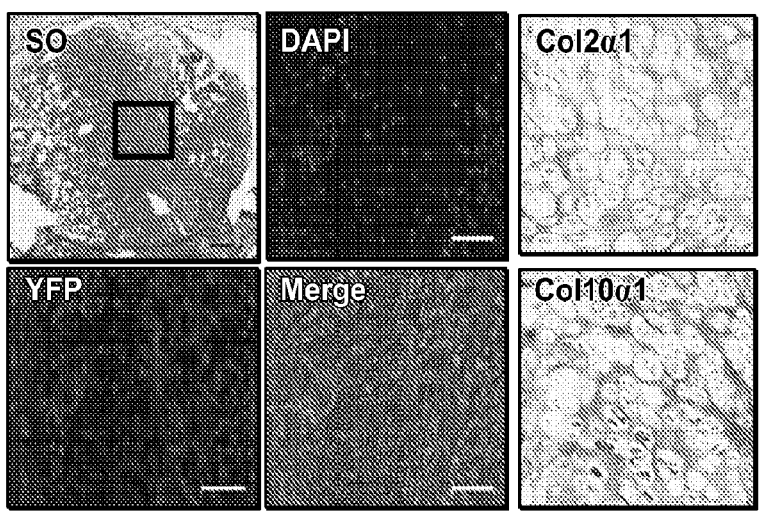

Next, we turned to lineage-tracing experiments using Rosa26lacZ (R26lacZ) or Rosa26YFP (YFP) Cre reporter mice. Remarkably, Ctsk-Cre, but not LysM-Cre, was expressed in a subset of perichondrial cells within the so-called "Groove of Ranvier" (FIG. 2a). Sections from knee joints collected at post-natal day 10 revealed significant expansion of a cluster of Alcian blue/Safranin O-positive cells in this region in Ctsk-KO, but not Ctsk-Control, mice (FIG. 2b, boxed region and FIG. 5a). By 2 weeks post-birth, the YFP+ cells had expanded and differentiated into ectopic cartilaginous tissue in compound Ctsk-KO/YFP reporter mice (FIG. 2c. boxed region). Exostoses from 12 week-old compound Ctsk-KO/YFP reporter mice consisted of YFP+ chondroid cells at various stages of development, as revealed by cell morphology and Col2α1 and Col10α1 immunostaining (FIG. 2d). Hence, cartilaginous tumors in Ctsk-KO mice (and, by analogy, most likely in MC) result from lack of Shp2 in Ctsk+ cells from the Perichondrial Groove of Ranvier.

Figure 3A:
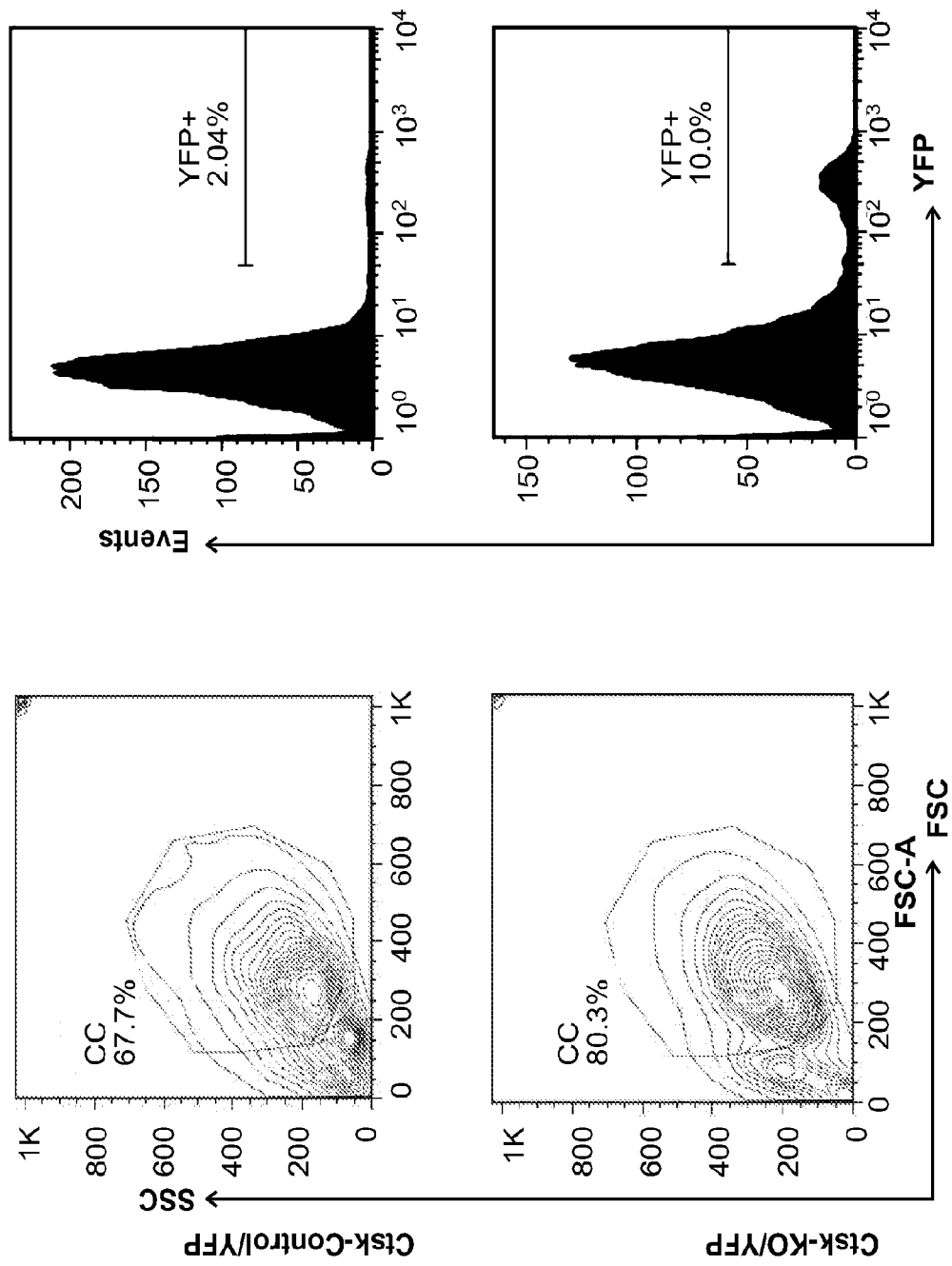
FIG. 3a is a graph showing the results of a flow cytometric analysis showing YFP+ cells from the epiphyseal cartilage of Ctsk-Control/YFP mice; note increased number of these cells in 2-week-old Ctsk-KO/YFP mice. CC: Chondroid cells.
Figure 3B:
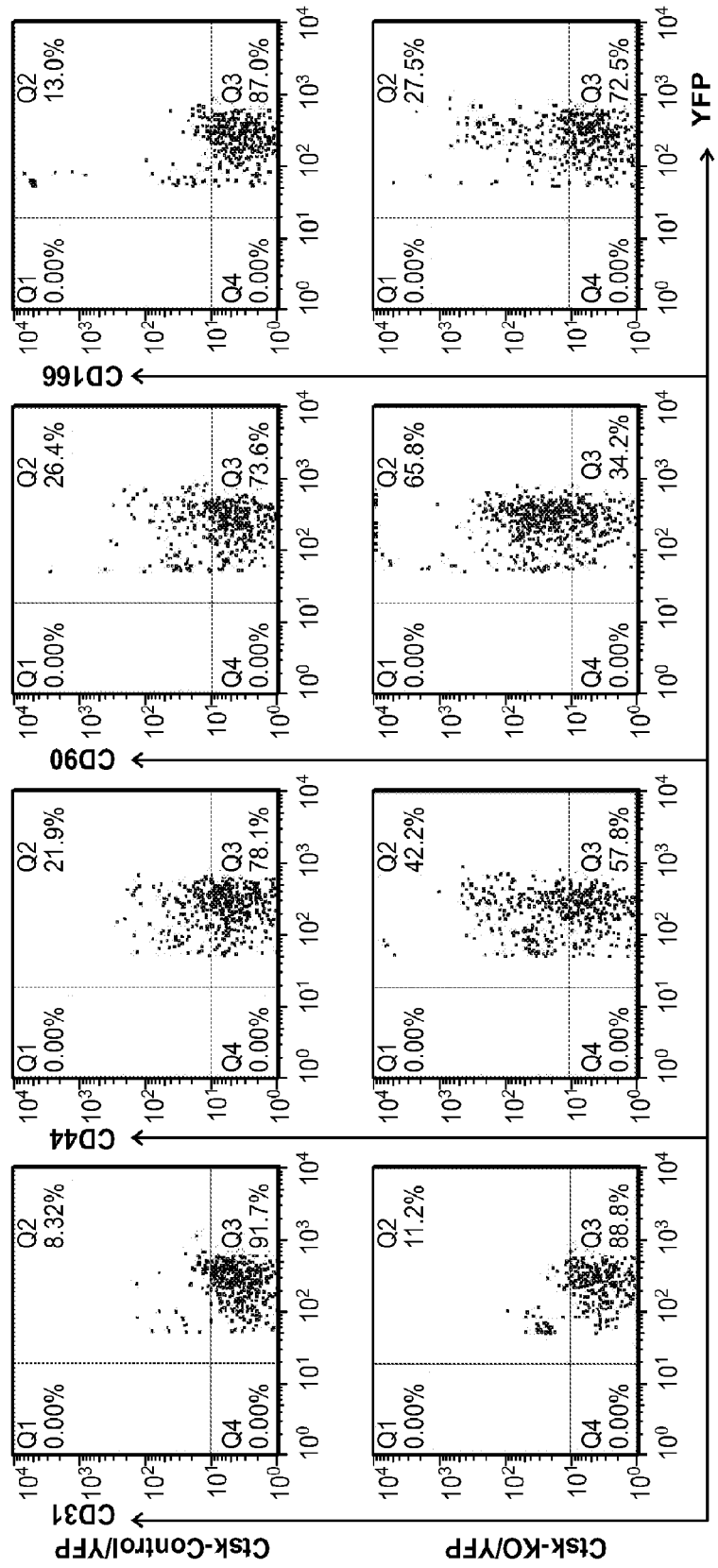
FIG. 3b is a graph showing the results of a flow cytometric analysis of YFP+ perichondrial cells showing staining for CD31, CD44, CD90, and CD166.
Figure 3C:
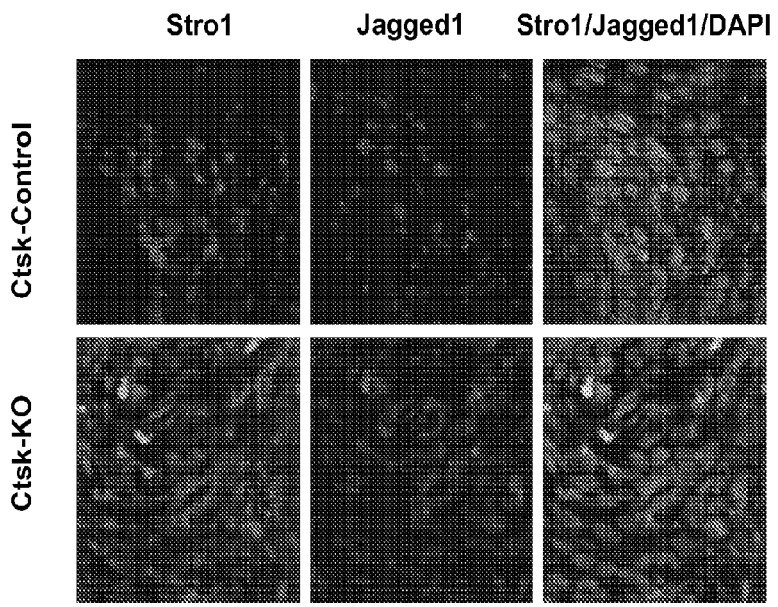
FIG. 3c is a photomicrograph showing immunofluorescence staining showing Stro1 and Jagged1 expression in YFP+ perichondrial cells. These data show that Ptpn11 deletion in Ctsk-expressing cells causes expansion of novel chondroprogenitor cell population within the Perichondrial Groove of Ranvier region.

The Perichondrial Groove of Ranvier is believed to contain chondroprogenitors responsible for circumferential cartilage growth, but these cells have not been well-characterized. We harvested epiphyseal cartilage cells from the distal femurs and proximal tibiae of Ctsk-Control/YFP and Ctsk-KO/YFP mice at P10-12, and analyzed them by flow cytometry. Compared with controls, the frequency of YFP+ cartilage cells from Ctsk-KO/YFP mice increased from by ~5-fold (FIG. 3a). Within the YFP+ cell population, the percentage of cells staining positive for CD44, CD90, and CD166, but not CD31, also increased (FIG. 3b). Furthermore, expression of Stro1 and Jagged1, two markers associated with chondroprogenitors within the Groove of Ranvier that retain a BrdU label was increased in the Perichondrial Groove of Ranvier of Ctsk-KO mice (FIG. 3c). Taken together, these data suggest that Shp2 regulates the proliferation of a novel cartilage cell population characterized by Ctsk expression, which we hereafter term "Ctsk+ Chondroid Progenitors" (CCPs).

Figure 4A:
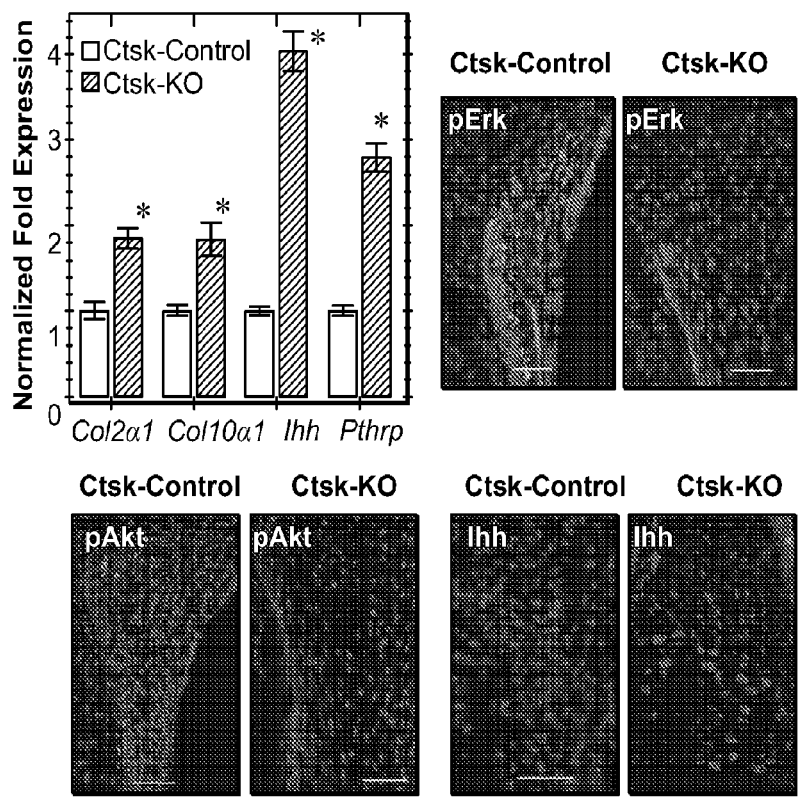
FIG. 4a, Left panel, is a bar graph of qPCR results showing increased Col2α1, Col10α1, Ihh, and Pthrp expression in laser-captured cartilaginous cells from exostoses, compared with normal articular cartilage cells (n=4, *p<0.05, Student t test).

Multiple signaling pathways tightly control cartilage development and homeostasis. Hedgehog and PTHRP signaling are particularly important, and aberrant regulation of these pathways causes developmental defects and skeletal tumors. We examined chondrogenic gene expression in cartilage tumors from Ctsk-KO mice by quantitative reverse-transcription PCR (q-PCR). Consistent with our immunostaining data (FIG. 2d), Col2α1 and Col10α1 transcripts were increased; in addition, Ihh and Pthrp levels were elevated substantially (FIG. 4a). These findings prompted us to examine whether and how Shp2 regulates Ihh and Pthrp. During development, cells within the perichondrium make Fgf, which can signal to adjacent cells via Fgfr3 to suppress Ihh expression. Given that Shp2 is required for Fgfr signaling in other cell types2,32, we hypothesized that Shp2 is required for Fgfr3 to suppress Ihh expression. To test this possibility, we assessed the activation state of Fgfr3 signaling components and Ihh expression in CCPs by immunostaining. Erk activation, as assayed by the phosphorylation of Tyr204Thr202, was compromised in the absence of Shp2, whereas Akt and Stat1/3 activation (based on the phosphorylation of Ser473 and Tyr807, respectively) were unaffected (FIG. 4a. Furthermore, consistent with our q-PCR data, Ihh expression was elevated in Shp2-deficient CCPs (FIG. 4a).

Figure 4B:
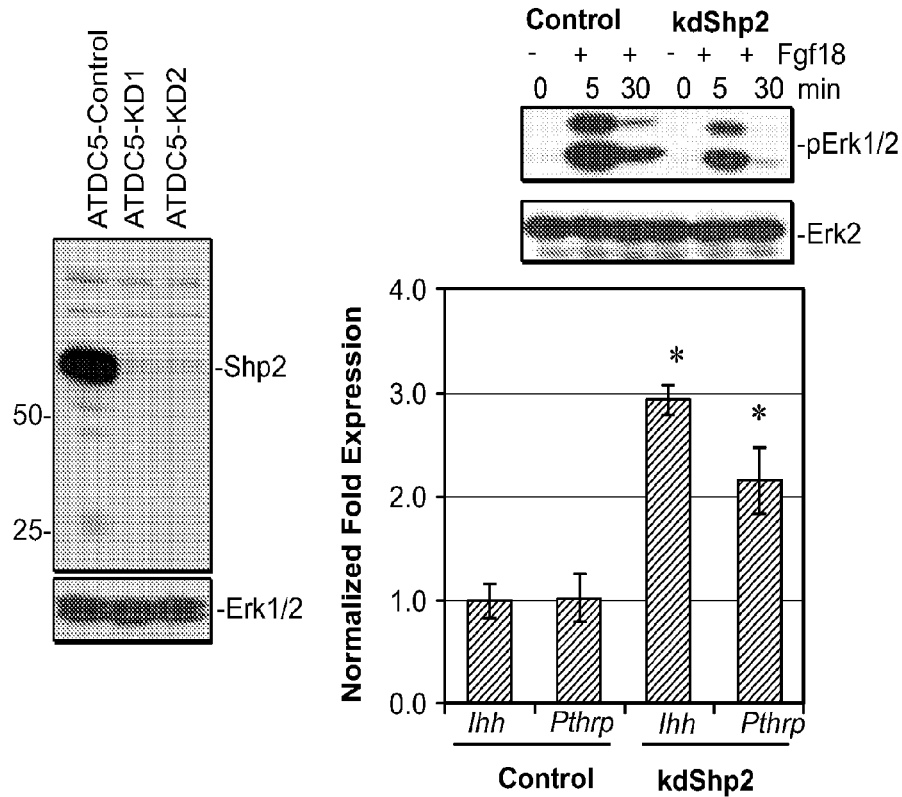
FIG. 4b, Left Panel, is a photograph of an immunoblot showing Shp2 levels in ATDC5 chondroprogenitor cell lines stably expressing shRNAs against murine Ptpn11 (ATDC5-KD1, ATDC5-KD2, respectively) or a scrambled control hairpin.
Figure 4C:
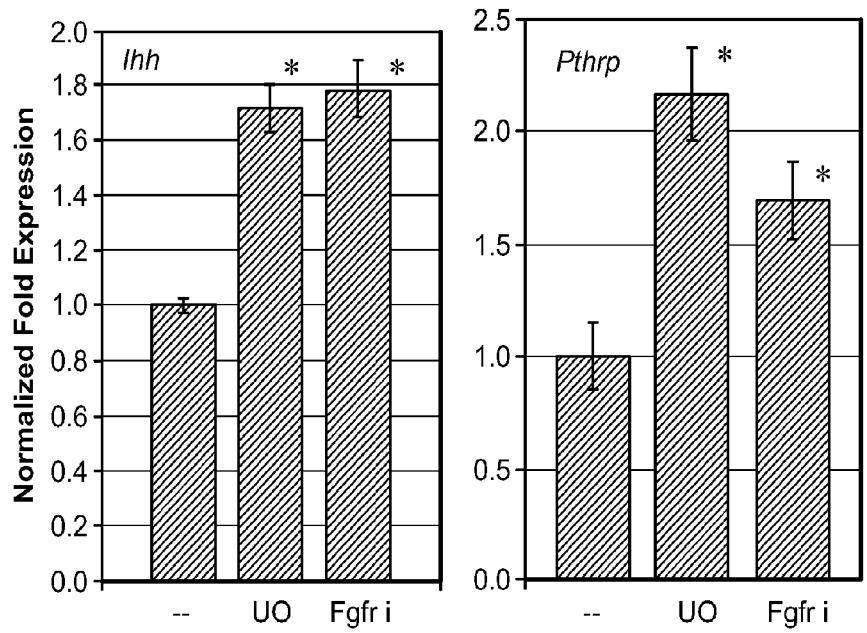
FIG. 4c is a bar graph showing that FGFR (PD173074, 10 nM) or MEK (UO126, 1 μM) inhibitor treatment of parental ATDC5 cells enhances Ihh and Pthrp expression, as shown by q-PCR (n=3, *p<0.05, Student t test).

CCPs are rare, rendering detailed biochemical analyses of these cells unfeasible. We therefore tested the effects of Shp2 depletion in ATDC5 chondroid cells by stably expressing either of two shRNAs directed against murine Ptpn11. As in Ctsk-KO mice (FIG. 4a), Fgf18-evoked Erk activation was decreased, while Ihh and Pthrp levels were increased, in Shp2 deficient-ATDC5 cells, compared with cells expressing an shRNA control (FIG. 4b). Conversely, FGFR (PD173074) or MEK (UO126) inhibitor treatment of randomly growing, parental ATDC5 cells led to enhanced Ihh and Pthrp expression (FIG. 4c).

Figure 4D:
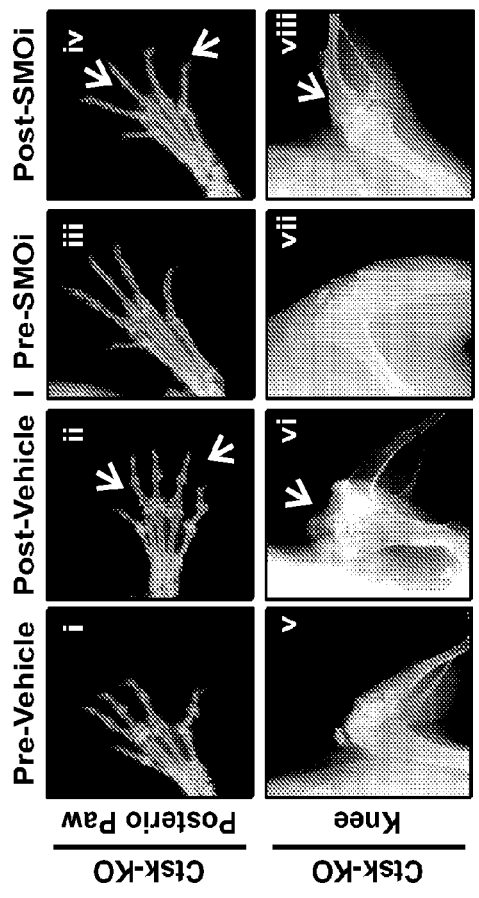
FIG. 4d is a series of Faxitron radiographs showing that blockade of the Hedgehog pathway by administration of the Smoothened inhibitor PF-04449913 (100 μg/g body weight) by daily gavage to Ctsk-KO mice (n=5) ameliorates tumor formation compared with vehicle control (0.5% methylcellulose)-treated mice. Images of representative posterior paws (i-iv) and knese (v-vii) taken pre-treatment (i, iii, v, vii) and post-treatment with vehicle (ii, vi) or Smoothened inhibitor (SMOi) (iv, viii) for 4 weeks. Note continued development of exostoses and endochromas in Vehicle-treated mice, and their amelioration in SMOi-treated group (arrows). Also, see FIGS. 7a,b and 8a,b. These data show that Shp2 deficiency compromises Erk activation but promotes Ihh and Pthrp expression.
Figure 7A:
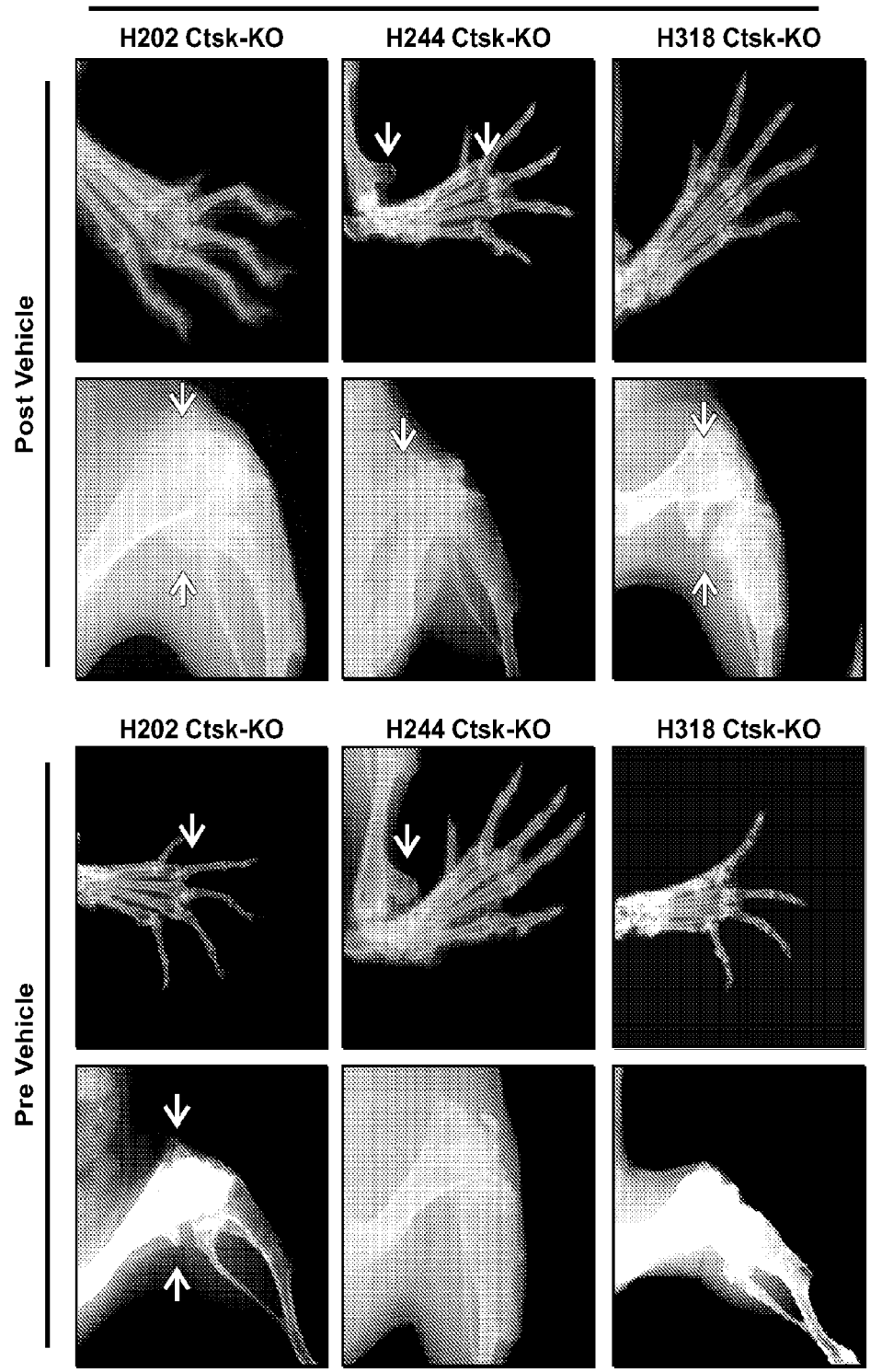
FIGS. 7a-b are a series of Faxitron radiographs showing that blockade of the Hedgehog pathway by administration of the Smoothened inhibitor (SMOi) PF-04449913 (100 μg/g body weight) or vehicle control (0.5% methylcellulose) by daily gavage to Ctsk-KO mice ameliorates tumor formation compared with vehicle alone treated mice. All animals used for these experiments are shown. Note the reduction of number and size of exostoses (arrows) in SMOi-, but not vehicle-treated Ctsk-KO mice (also see FIG. 8a,b). SMOi was administered by oral gavage to Ctsk-KO mice beginning at post-natal week 5 for four weeks, and mice were euthanized at week 9.
Figure 7B:
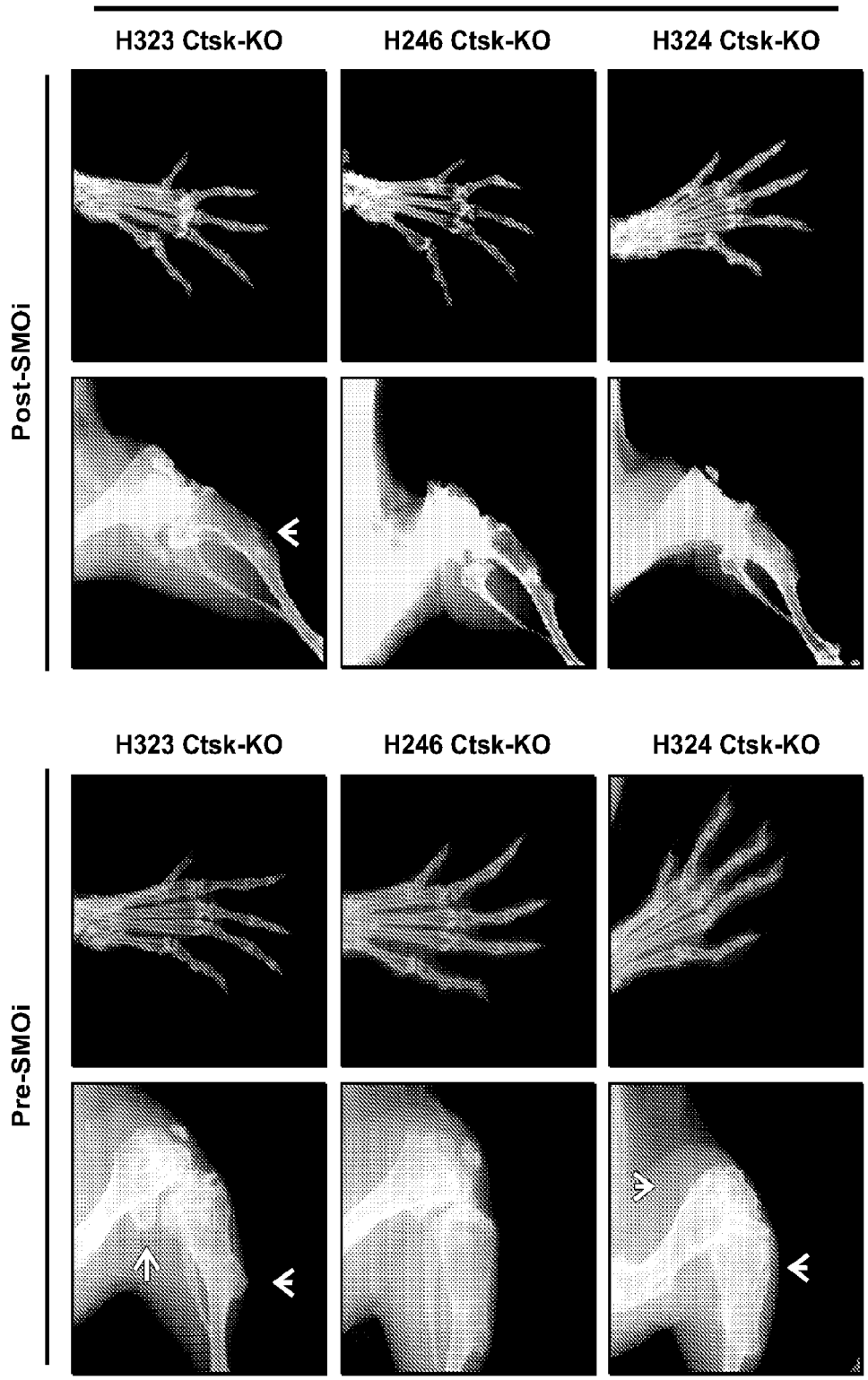
Figures 8A, 8B:
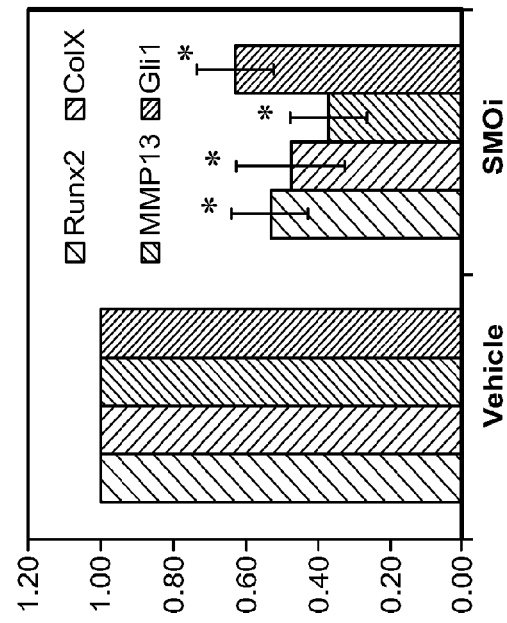
FIG. 8a is a series of charts showing number and size of exostoses in Ctsk-KO mice post-treatment (n=5) with vehicle or Smoothened inhibitor (SMOi). Note decrease in average number of exostoses/per paw, knee, and tibiae (n=10). # indicates that only small exostoses were observed. p value was determined by Student t test.
FIG. 8b is a bar graph of qPCR results showing that oral administration of the Smoothened inhibitor SMOi to wild type mice for 1 week blunts the expression of Col2α1, Col10α1, Mmp13 and Gli1 in epiphyseal cartilage (n=3, *p<0.05, student t test).
Figure 9D:
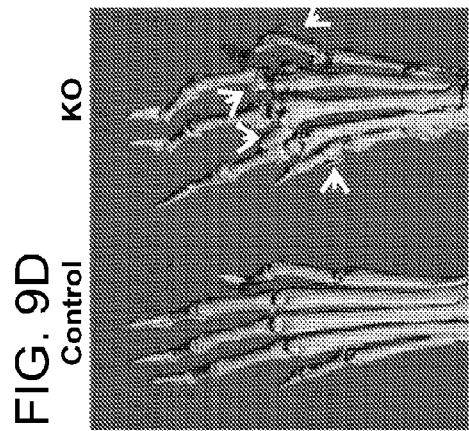
FIGS. 9A-F are a series of photographs, a bar graph and schematic showing that inhibition of hedgehog signaling by oral administration of an inhibitory agent leads to prevention and inhibition of the development of exostosis and enchondromas.
Figure 9C:
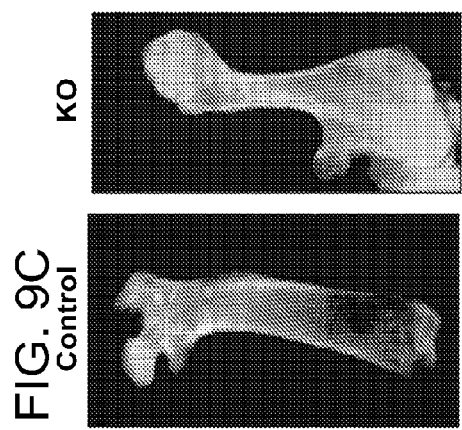
Figure 9A:
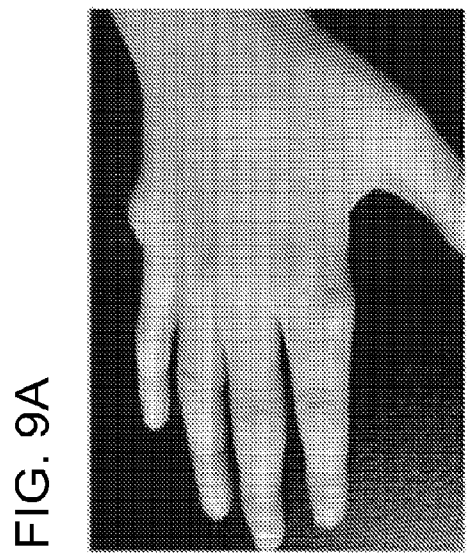
Figure 9E:
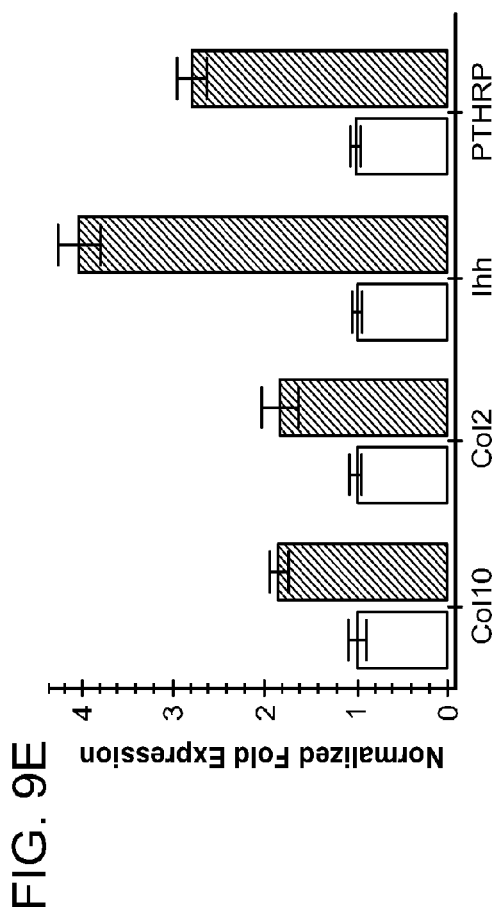
Figure 9B:
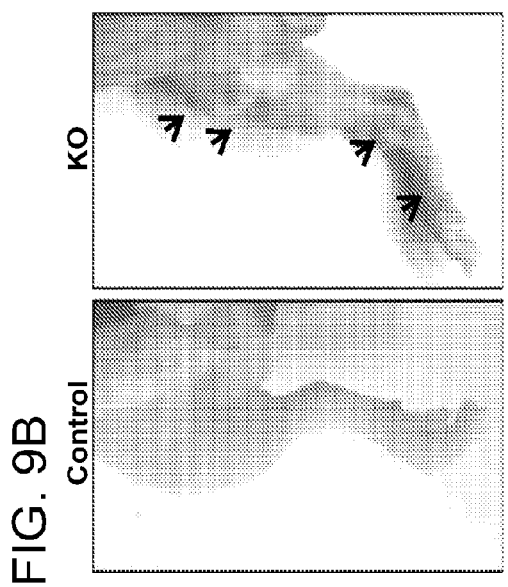
Figure 9F:
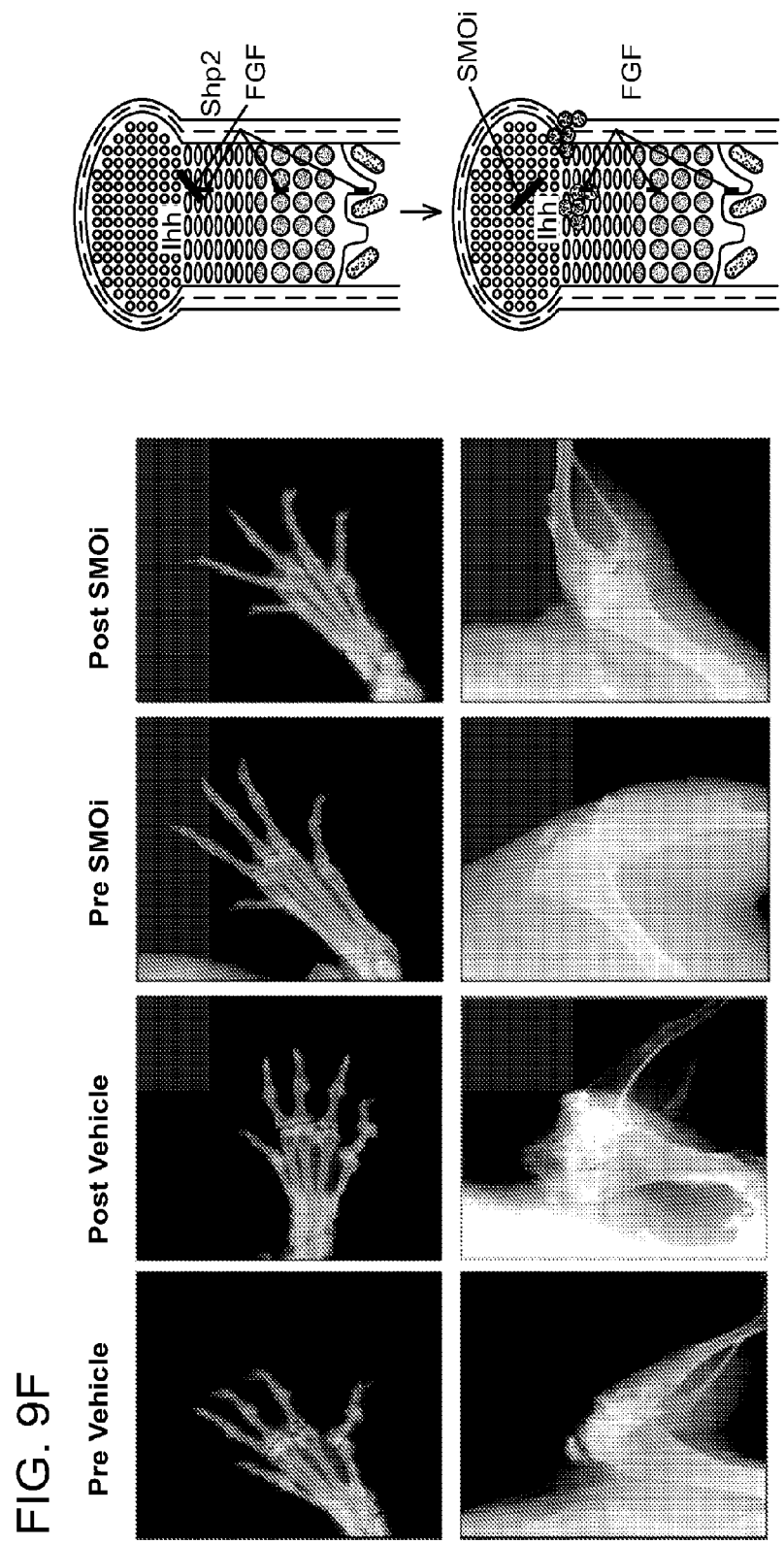

Ihh signaling leads to Pthrp production. Hence, our data, along with previous studies, suggested that increased Ihh levels might play a crucial role in MC pathogenesis. If so, then blocking or attenuating Ihh signaling might slow and/or prevent MC development. To test this hypothesis, Control (wild type) and Ctsk-KO mice (5/group) were treated with the Smoothened inhibitor PF-04449913 (100 µg/g body weight) or vehicle control (0.5% methylcellulose) by daily gavage, beginning at 5 weeks of age and continuing for the succeeding 4 weeks. The skeletal phenotype was examined by X-ray, µ-CT, and histological analysis at the end of experiment. Remarkably, Smoothened inhibitor treatment significantly reduced the number (FIG. 4d, 7a-b, 8a-b) and size of exostoses (FIG. 4d, 7a-b) and improved the function of multiple joints.

The data indicate that MC results from loss of SHP2 specifically in CCPs, a heretofore poorly characterized cell population within the Perichondrial Groove of Ranvier, which is believed to function as a stem cell niche for joints and as a reservoir for the germinal layer cells of the growth plate. Cells within the Groove of Ranvier express high levels of FGFR3, and removal of these cells prevents longitudinal bone growth. Groove of Ranvier cells can migrate along and reside in articular cartilage, implicating them in the maintenance of articular cartilage homeostasis and possibly in the pathogenesis of degenerative joint diseases, such as osteoarthritis. YFP+ cells were also observed in the articular cartilage of normal mice in our lineage tracing experiments. SHP2, acting downstream of FGFR3 and upstream of the canonical RAS/ERK pathway, regulates CCP proliferation and chondrogenic differentiation. Consequently, PTPN11 deficiency in these cells causes excessive proliferation, chondrogenic differentiation, and cartilage tumorigenesis.

MC is associated with heterozygous inactivating mutations in PTPN11, yet Ptpn11fl/+; CtskCre mice are normal, whereas Ctsk-KO mice display a MC-like syndrome. Although it is formally possible that PTPN11 gene dosage effects differ in mouse and man (and thus 50% reduction in SHP2 levels causes MC in humans but not in mouse), we think it is far more likely that loss of the remaining PTPN11 allele (e.g., by LOH or silencing) is required to cause cartilage tumors in MC. If so, then unlike its oncogenic role in JMML, other hematologic malignancies and solid tumors, PTPN11 acts as a classic tumor suppressor gene in cartilage. It has been reported that liver-specific Ptpn11 deletion results in hepatocellular carcinoma. However, we have not observed any liver tumors in our Ptpn11 conditional knockout mice crossed to the same Cre line, nor is PTPN11 clearly implicated in the pathogenesis of human hepatocellular carcinoma. Moreover, our biochemical and pharmacological analysis, together with previous studies, provide an explanation for the apparently paradoxical pro- and anti-oncogenic effects of PTPN11. In both cases, SHP2 is a critical regulator of ERK activation. The activating PTPN11 mutations associated with cancer promote proliferation and survival at least in part via increased ERK activation. Similarly, over-expression or increased activation of normal SHP2 binding proteins such as GAB2, or the presence of pathologic SHP2 binding proteins such as H. pylori CagA, can hyperactivate ERK and contribute to various malignancies. Conversely, SHP2 deficiency is oncogenic in CCPs because in these cells, ERK normally represses the expression of the growth stimulator IHH (which in turn, promotes PTHRP production). Given the mechanism of MC pathogenesis described herein, the results argue for caution in the long term use of MEK and ERK inhibitors.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference.

All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for preventing, slowing, or blocking the formation of an exostosis or an enchondroma comprising administering to an animal a hedgehog pathway inhibitor, wherein said animal comprises metachondromatosis and wherein said animal comprises a mutation in a gene encoding Src-homology 2 domain-containing phosphatase 2 (SHP2) in cartilage.

2. The method of claim 1, wherein said inhibitor comprises a Smoothened inhibitor.

3. The method of claim 2, wherein said inhibitor comprises PF04449913.

4. The method of claim 1, wherein said inhibitor is selected from the group consisting of PF04449913, Cyclopamine ($C_{27}H_{41}NO_2$), Jervine ($C_{27}H_{39}NO_3$), IPI-926/saridegib, GDC-0449/vismodegib, LDE-225/erismodegib, TAK-441, BMS-833923, SANT 74-75, and SANT 1-4.

5. The method of claim 1, wherein said inhibitor is administered systemically.

6. The method of claim 1, wherein said inhibitor is administered locally to a diseased site.

7. The method of claim 1, wherein the formation of an exostosis is blocked.

8. The method of claim 1, wherein the formation of an enchondroma is blocked.

9. The method of claim 1, wherein the formation of an exostosis is slowed.

10. The method of claim 1, wherein the formation of an enchondroma is slowed.

11. The method of claim 1, wherein the animal is a human, mouse, dog, cat, or horse.

12. The method of claim 11, wherein the animal is a human.

13. The method of claim 1, wherein said animal has not been diagnosed with malignant chondrosarcoma.

\* \* \* \* \*

SEQUENCE LISTING

```
<160> NUMBER OF SEQ ID NOS: 2

<210> SEQ ID NO 1
<211> LENGTH: 64
<212> TYPE: DNA
<213> ORGANISM: Artificial Sequence
<220> FEATURE:
<223> OTHER INFORMATION: Oligo

<400> SEQUENCE: 1
gatccccgat tcagaacact ggggacttca agagagtccc cagtgttctg aatcttttg      60 gaaa                                                                  64

<210> SEQ ID NO 2
<211> LENGTH: 64
<212> TYPE: DNA
<213> ORGANISM: Artificial Sequence
<220> FEATURE:
<223> OTHER INFORMATION: Oligo
```

-continued

```
<400> SEQUENCE: 2
gatccccgat tcagaacact ggggacttca agagagtccc cagtgttctg aatctttttg    60
gaaa                                                                 64
```